US011857487B2

(12) United States Patent
Oppenheimer et al.

(10) Patent No.: US 11,857,487 B2
(45) Date of Patent: *Jan. 2, 2024

(54) ELECTRONIC DEVICES FOR ASSISTING PERFORMANCE OF MEDICAL PROCEDURES

(71) Applicant: Ximio Health Inc., Wilmington, DE (US)

(72) Inventors: Beno Oppenheimer, New York, NY (US); Michael Dibenedetto, Worcester, MA (US)

(73) Assignee: Ximio Health Inc., Wilmington, DE (US)

( * ) Notice: Subject to any disclaimer, the term of this patent is extended or adjusted under 35 U.S.C. 154(b) by 1088 days.

This patent is subject to a terminal disclaimer.

(21) Appl. No.: 16/537,948

(22) Filed: Aug. 12, 2019

(65) Prior Publication Data

US 2020/0100983 A1  Apr. 2, 2020

Related U.S. Application Data

(63) Continuation of application No. 14/980,141, filed on Dec. 28, 2015, now Pat. No. 10,376,441.

(51) Int. Cl.
*A61H 31/00* (2006.01)
*G06F 1/16* (2006.01)
(Continued)

(52) U.S. Cl.
CPC ......... *A61H 31/007* (2013.01); *A61H 31/005* (2013.01); *G06F 1/163* (2013.01);
(Continued)

(58) Field of Classification Search
CPC ................ A61H 31/007; A61H 31/005; A61H 2201/0188; A61H 2201/5007;
(Continued)

(56) References Cited

U.S. PATENT DOCUMENTS 5,239,988 A  8/1993  Swanson
8,676,313 B2  3/2014  Volpe et al.
(Continued)

FOREIGN PATENT DOCUMENTS

WO  WO 2017/117098  7/2017

OTHER PUBLICATIONS

International Search Report and Written Opinion for Int. App. No. PCT/US2019/039728, dated Nov. 6, 2019 (15 pages).
(Continued)

*Primary Examiner* — Quang D Thanh
(74) *Attorney, Agent, or Firm* — Fish & Richardson P.C.

(57) ABSTRACT

An example system includes a first wearable computing device, and at least one additional wearable computing device. The first wearable computing device is configured to retrieve information regarding a series of tasks to be performed in treating a patient in cardiopulmonary arrest. The information includes, for each task, an indication of a user to perform the task, an indication of a time point to perform the task. The first wearable computing device is further configured identify one or more subsets of the information, and transmit each subset to a different corresponding one of the additional wearable computing devices. Each additional wearable computing device is configured to receive, from the first wearable computing device, at least one of the one or more subsets of the information, and output, for each task within a received subset, a corresponding prompt to perform the task at the respective time point associated with the task.

39 Claims, 22 Drawing Sheets

(51) Int. Cl.
*G16H 40/60* (2018.01)
*G16H 50/30* (2018.01)
*G16H 20/40* (2018.01)
*G16H 40/63* (2018.01)

(52) U.S. Cl.
CPC ............ *G16H 20/40* (2018.01); *G16H 40/60* (2018.01); *G16H 40/63* (2018.01); *G16H 50/30* (2018.01); *A61H 2201/0188* (2013.01); *A61H 2201/5007* (2013.01); *A61H 2201/5043* (2013.01); *A61H 2201/5048* (2013.01); *A61H 2201/5061* (2013.01); *A61H 2201/5071* (2013.01); *A61H 2201/5084* (2013.01); *A61H 2201/5089* (2013.01); *A61H 2201/5097* (2013.01); *A61H 2230/205* (2013.01); *A61H 2230/207* (2013.01); *A61H 2230/25* (2013.01)

(58) Field of Classification Search
CPC .... A61H 2201/5043; A61H 2201/5048; A61H 2201/5061; A61H 2201/5071; A61H 2201/5084; A61H 2201/5089; A61H 2201/5097; A61H 2230/205; A61H 2230/207; A61H 2230/25; G06F 1/163; G16H 20/40; G16H 40/60; G16H 40/63; G16H 50/30
See application file for complete search history.

(56) References Cited

U.S. PATENT DOCUMENTS

| | | | |
|---|---|---|---|
| 9,028,259 B2 | 5/2015 | Centen et al. | |
| 10,376,441 B2* | 8/2019 | Oppenheimer | ........ G16H 20/40 |
| 2004/0162510 A1 | 8/2004 | Jayne et al. | |
| 2004/0162587 A1* | 8/2004 | Hampton | ........... A61N 1/39044 601/44 |
| 2006/0270952 A1 | 11/2006 | Freeman | |
| 2008/0097534 A1 | 4/2008 | Myklebust et al. | |
| 2008/0171311 A1 | 7/2008 | Centen et al. | |
| 2012/0089054 A1 | 4/2012 | Centen et al. | |
| 2012/0330200 A1 | 12/2012 | Voss | |
| 2013/0310718 A1* | 11/2013 | Jensen | ................ A61H 31/005 601/41 |
| 2014/0272860 A1 | 9/2014 | Peterson et al. | |
| 2014/0342330 A1* | 11/2014 | Freeman | .............. G09B 23/288 434/265 |
| 2015/0087919 A1 | 3/2015 | Johnson et al. | |
| 2015/0224021 A1 | 8/2015 | Centen et al. | |
| 2017/0079537 A1 | 3/2017 | McEwen | |
| 2017/0181925 A1 | 6/2017 | Oppenheimer et al. | |

OTHER PUBLICATIONS

Boyle et al., *Scanning laser Doppler is a useful technique to assess foot cutaneous perfusion during femoral artery cannulation*, Critical Care, 3(4):95-100 (1999).

Gonzalez-Otero et al., *A New Method for Feedback on the Quality of Chest Compressions during Cardiopulmonary Resuscitation*, Hindawi Publishing Corporation, BioMed Research International, vol. 2014, Article ID 865967, 1-7 (2014).

Tekscan.com [online], Comparison of Interface Pressure Measurement Options, retrieved on Aug. 13, 2008 (22 pages).

International Search Report and Written Opinion for Int. App. No. PCT/US2016/068658, dated Mar. 27, 2017 (15 pages).

* cited by examiner

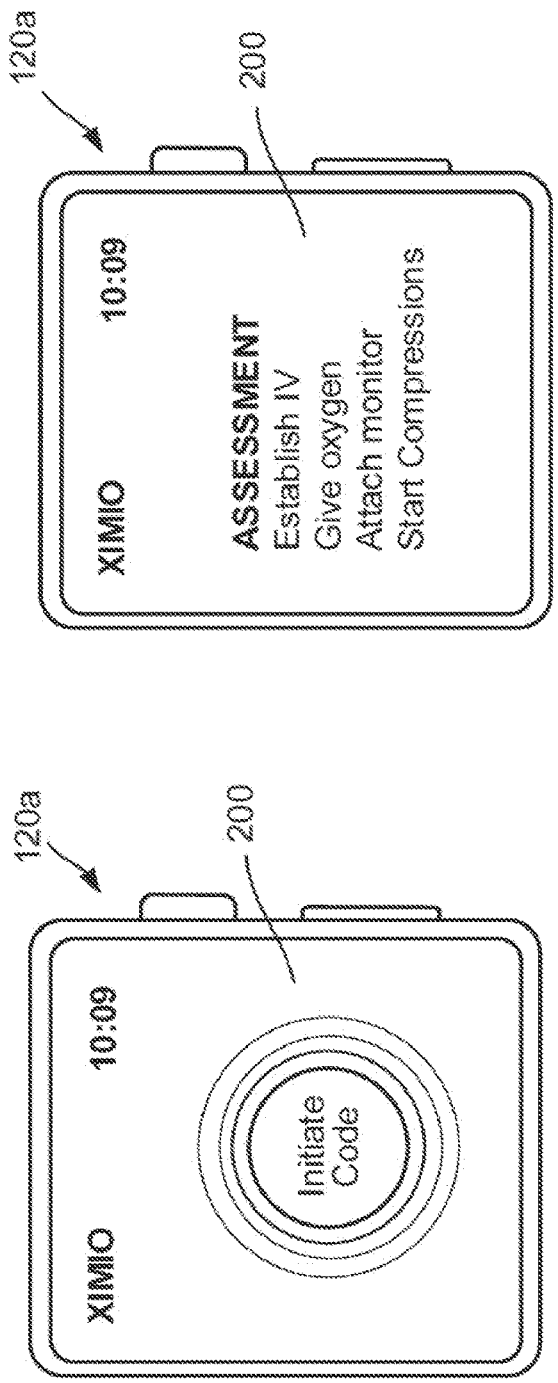
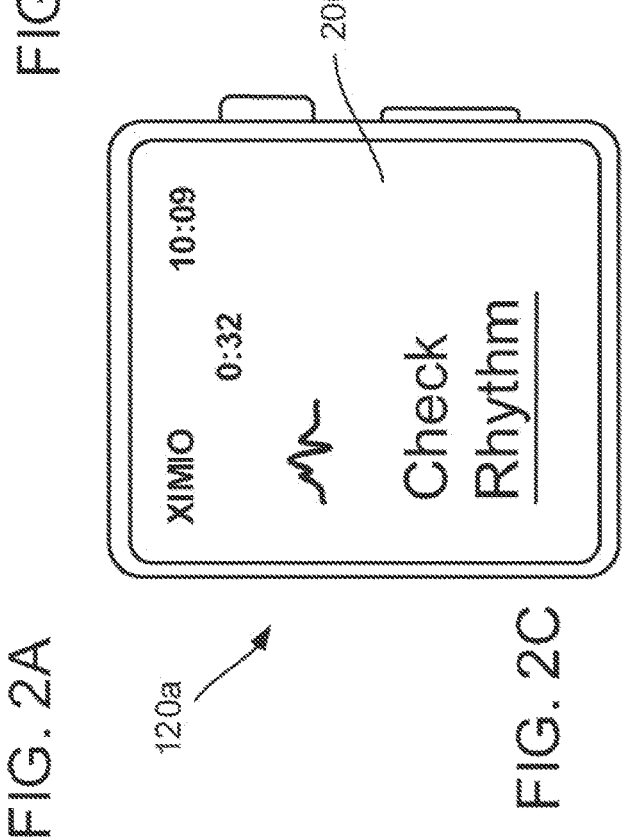
FIG. 2A
FIG. 2B
FIG. 2C

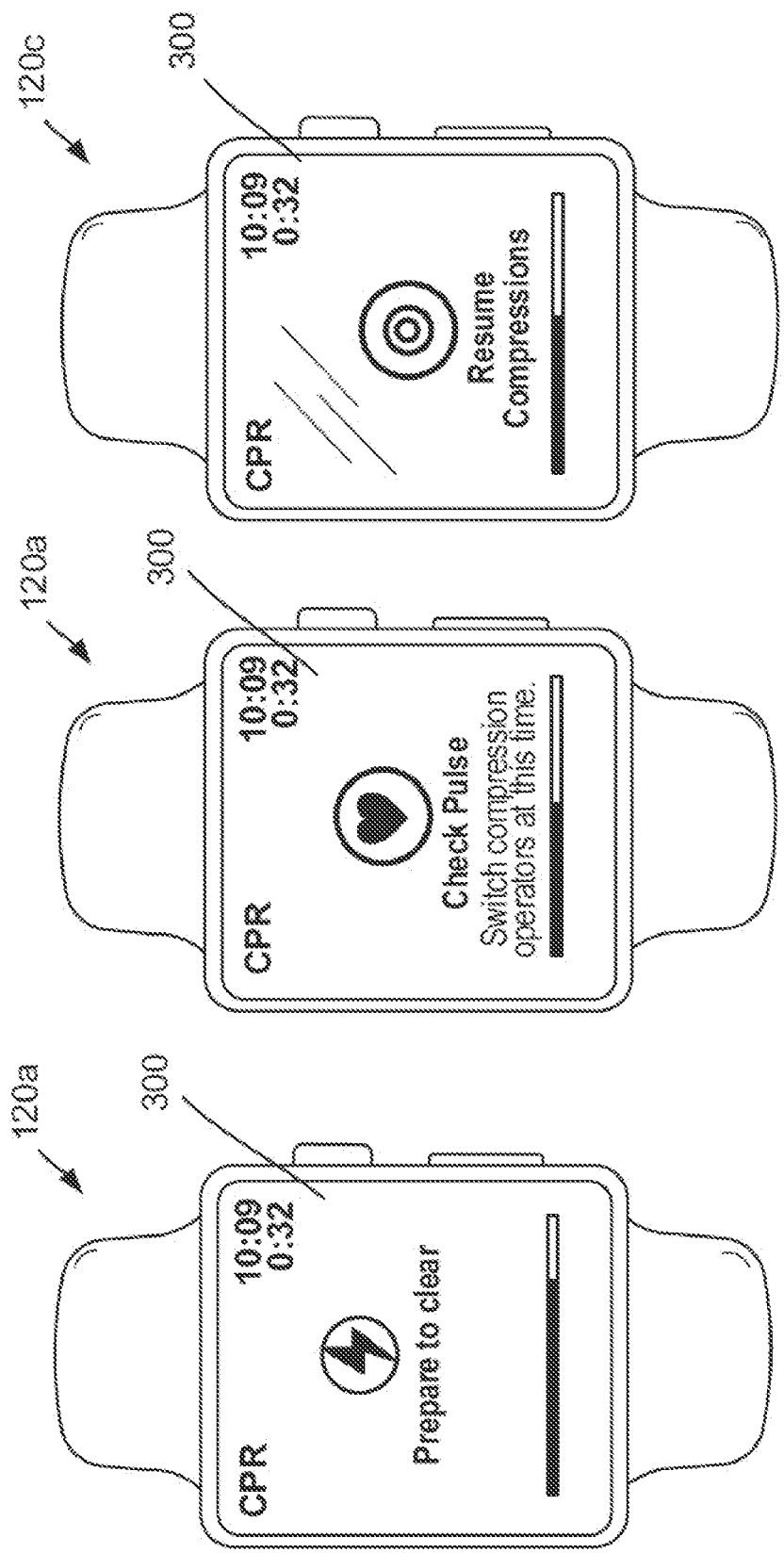

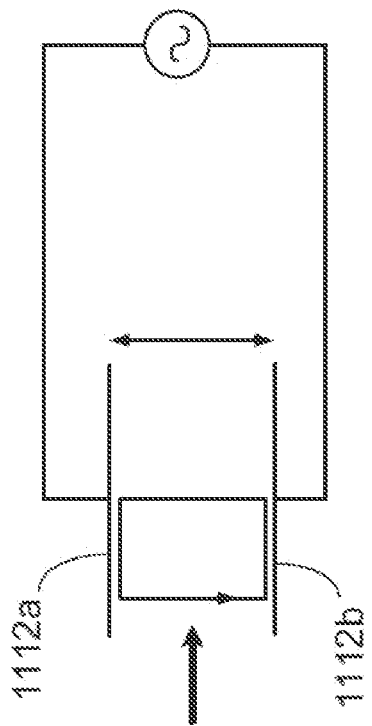
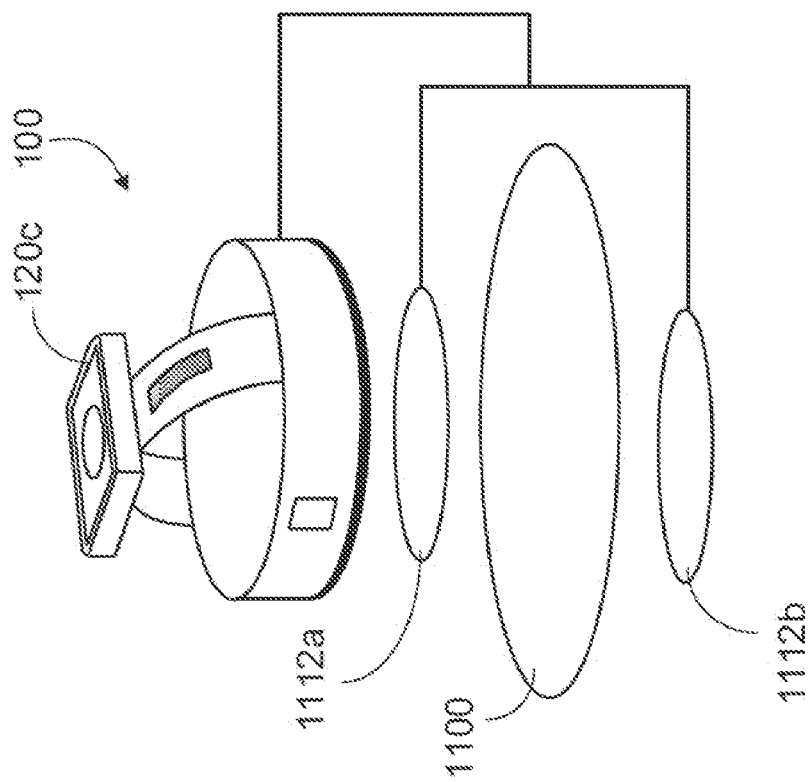
FIG. 11D
FIG. 11C

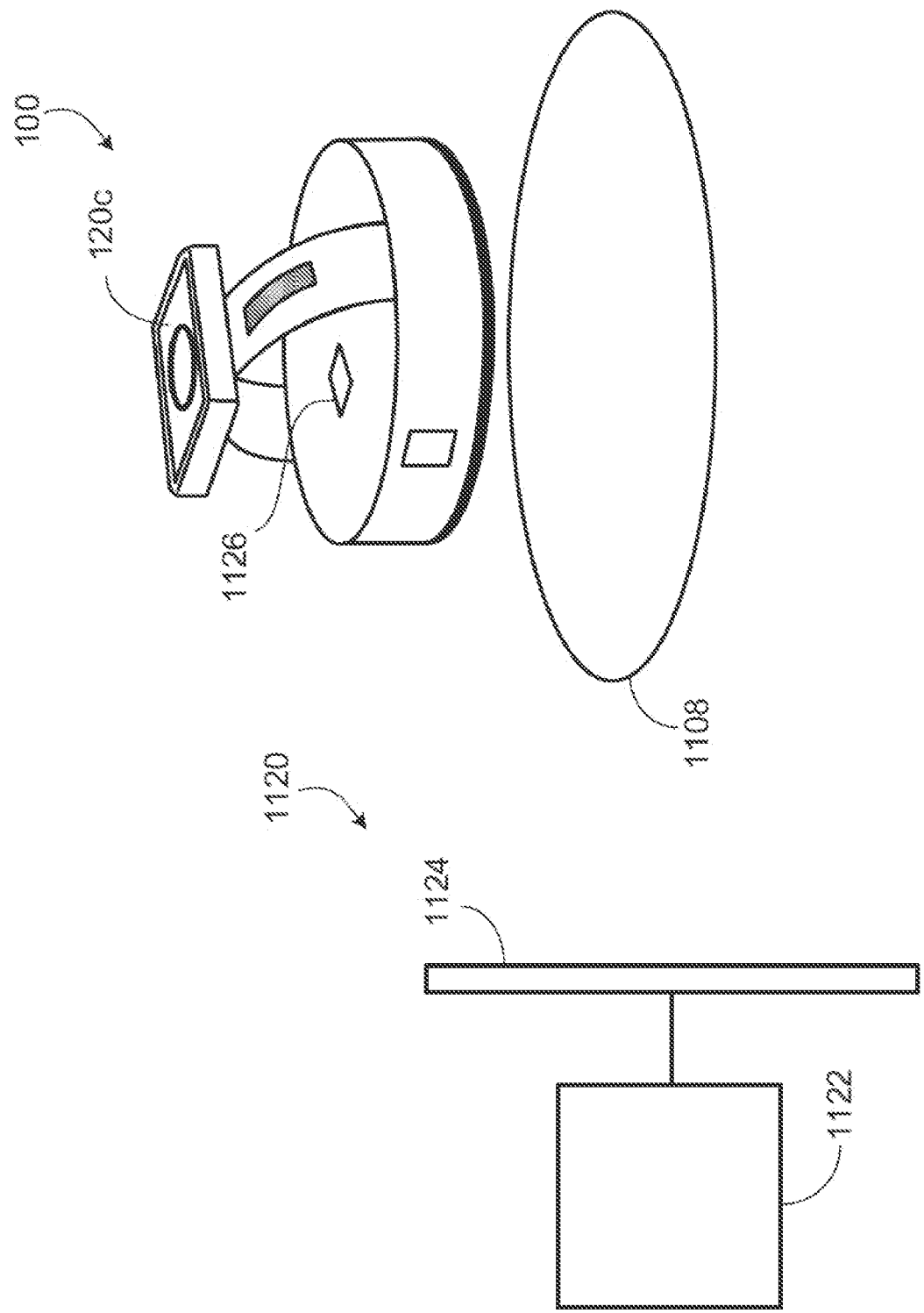

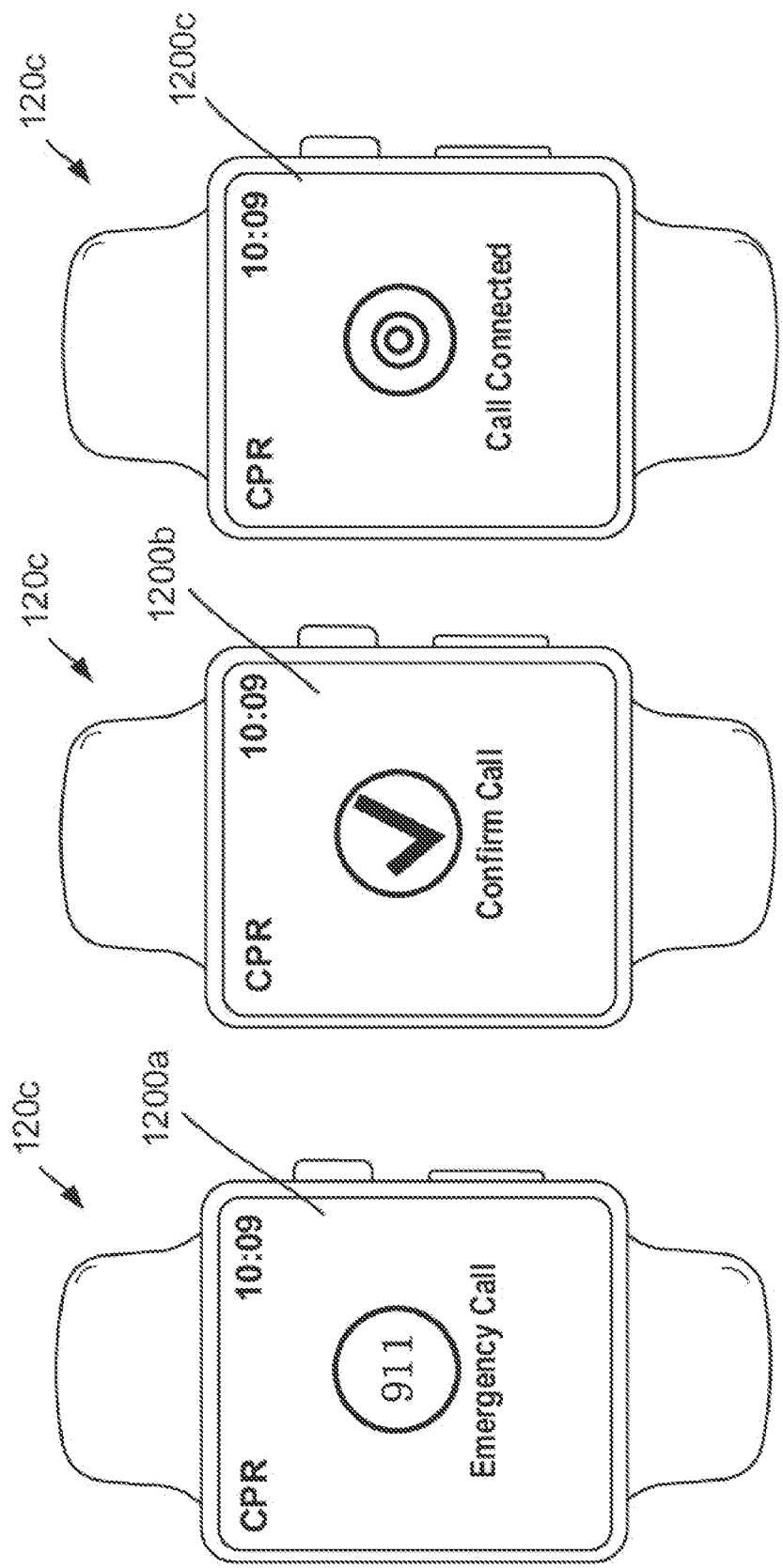

ELECTRONIC DEVICES FOR ASSISTING PERFORMANCE OF MEDICAL PROCEDURES

CROSS-REFERENCE TO RELATED APPLICATIONS

This application is a continuation and claims priority to U.S. application Ser. No. 14/980,141, filed on Dec. 28, 2015, which is incorporated by reference herein in its entirety.

TECHNICAL FIELD

This disclosure relates to electronic devices for assisting users in performing medical procedures.

BACKGROUND

Cardiac arrest, also known as cardiopulmonary arrest or circulatory arrest, is a sudden stop in effective blood circulation due to the failure of the heart to contract effectively or at all. Cardiac arrest is often treated via attempts at resuscitation. However, due to the acuity of these situations, the patient's outcome depends greatly on the good decision making and the timing of his caretakers.

To improve the likelihood of success, caretakers often follow guidelines for decision making and timing of interventions. For example, the American Heart Association has created intervention guidelines called the Advanced Cardiac Life Support (ACLS) protocols. Many hospitals mandate that providers be trained in these life-saving protocols.

SUMMARY

In general, in an aspect, a system includes a first wearable computing device, and at least one additional wearable computing device. The first wearable computing device is configured to retrieve information regarding a series of tasks to be performed in treating a patient in cardiopulmonary arrest. The information regarding the series of tasks includes, for each task, an indication of a user to perform the task, an indication of a time point to perform the task. The first wearable computing device is further configured identify one or more subsets of the information regarding the series of tasks, and transmit each subset to a different corresponding one of the additional wearable computing devices. Each additional wearable computing device is configured to receive, from the first wearable computing device, at least one of the one or more subsets of the information, and output, for each task within a received subset, a corresponding prompt to perform the task at the respective time point associated with the task.

Implementations of this aspect can include one or more of the follow features.

In some implementations, a first one of the two additional wearable computing device can be configured to receive an indication that a particular task has been performed at a particular time; and responsive to receiving the indication that the particular task has been performed at the particular time, record a time entry based on the particular task and the particular time, and transmit the time entry to the first wearable computing device.

In some implementations, receiving the indication that the particular task has been performed at the particular time can include receiving a user input indicating that the particular task has been performed.

In some implementations, the first one of the additional wearable computing devices can be further configured to receive an indication of a performance parameter associated with the particular task; and responsive to receiving the indication of the performance parameter associated with the particular task, record the performance parameter, and transmit the time entry to the first wearable computing device.

In some implementations, a first one of the additional wearable computing devices can include a pad, a pressure sensor, an electronic control module in communication with the pressure sensor, and a support securing the electronic control module above the pad, such that a first space is defined between the pad and the electronic control module. The first one of the additional wearable computing device can be configured to obtain, a pressure measurement, determine, based on the pressure measurement, a compressive force applied by the first one of the additional wearable computing device, and transmit a value representative of the compressive force to the first wearable computing device. In some cases, the pressure sensor can be embedded within the pad. In some cases, the first one of the additional wearable computing device can be configured to allow a user to place one or more hands into the first space to apply force onto the pad.

In some implementations, one or more of the additional mobiles devices can include a sensor, and an electronic control module in communication with the sensor. The electronic control module can be configured to obtain, following the output of the prompt within the received subset, a measurement signal from the sensor, and transmit the measurement signal to the first wearable computing device or to another one of the additional wearable computing devices. In some cases, the sensor is a capnometer, and the measurement signal indicates a concentration of carbon dioxide exhaled by the patient. In some cases, the sensor is an oxygen sensor, and the measurement signal indicates an oxygen perfusion of the patient.

In some implementations, retrieving information regarding the series of tasks can include selecting the series of tasks from among a plurality of series of tasks. In some cases, the series of tasks is selected from among the plurality of series of tasks based on a user input identifying a medical condition of the patient.

In some implementations, the first wearable computing mobile device can be configured to retrieve information regarding the series of tasks from a computer system communicatively coupled to the first wearable computing device.

In some implementations, the series of tasks can include one or more of a set consisting of: measurement of a pulse of the patient, administration of a drug to the patient, performance of chest compressions on the patient, and performance of a defibrillating shock to the patient.

In some implementations, the information regarding the series of tasks can include, for each task, a description of the task, and instructions for performing the task.

In some implementations, the first wearable computing device can be further configured to determine a performance quality index based on information received from the one of the additional wearable computing devices. The information can include at least one of a compression rate, a compression pressure, a pressure decay, a compression depth, and a compression rate variability associated with treating the patient.

In general, in another aspect, a cardiopulmonary resuscitation (CPR) device includes a pad, a pressure sensor, an electronic control module in communication with the pressure sensor, and a support securing the electronic control module above the pad, such that a first space is defined between the pad and the electronic control module. The CPR device is configured to obtain, from the pressure sensor a pressure measurement, determine, based on the pressure measurement, a compressive force applied onto the pad in a direction from the first space towards the pad, present, using the electronic control module, information regarding the compressive force to the user, and transmit, using the electronic control module, an indication of the compressive force over a communications network.

Implementations of this aspect can include one or more of the follow features.

In some implementations, the CPR device can be further configured to present, using the electronic control module, instructions for performing one or more tasks for treating a patient in cardiopulmonary arrest.

In some implementations, the CPR device can be further configured to transmit, over a communications network, a request for assistance in treating a patient in cardiopulmonary arrest.

In some implementations, the CPR device can be further configured to receive an indication that a particular task for treating a patient in cardiopulmonary arrest has been performed at a particular time; and responsive to receiving the indication that the particular task has been performed at the particular time, record a time entry based on the particular task and the particular time.

One or more of the implementations herein can provide various benefits. For example, in some cases, implementations of the electronic system can improve the likelihood of successfully treating a patient in cardiac arrest by allowing caretakers to coordinate their efforts when treating the patient in cardiac arrest. The electronic system can provide each user with a clear indication of his role in an intervention team, provide information regarding what tasks to perform and when to perform those tasks, and provide feedback regarding the effectiveness of his performance. Further still, the electronic system can provide information to caretakers when treating a patient, without requiring that the caretakers hold a device, book, or other object while doing so. Thus, the electronic system allows caretakers to treat the patient more effectively, and while having full use of their hands. Further, the electronic system can provide team management information to one or more users (e.g., a team leader), such that important information regarding the patient's care and the efforts of the users is readily accessible to an overseer. Further still, the electronic system can accurately record information regarding the patient's care, including the patient's vital signs, the tasks that were performed in treating the patient, and the time at which those tasks were performed. Thus, accurate records of the treatment can be subsequently reviewed during debriefings or other retrospective applications. Further still, the electronic system can be used as an education tool to instruct users in proper treatment techniques and protocols.

The details of one or more embodiments are set forth in the accompanying drawings and the description below. Other features and advantages will be apparent from the description and drawings, and from the claims.

BRIEF DESCRIPTION OF THE DRAWINGS

FIGS. 2A-2G are diagrams of example graphical user interfaces presented by a wearable computing device.

FIGS. 3A-3C are diagrams of example graphical user interfaces presented by a wearable computing device.

FIGS. 11C-11D are diagrams of another example system for measuring the compression depth of a rescuer's chest compressions on a patient.

FIG. 11E is a diagram of another example system for measuring the compression depth of a rescuer's chest compressions on a patient.

FIGS. 12A-12C are diagrams of example graphical user interfaces presented by a wearable computing device.

DETAILED DESCRIPTION

Figure 1A:
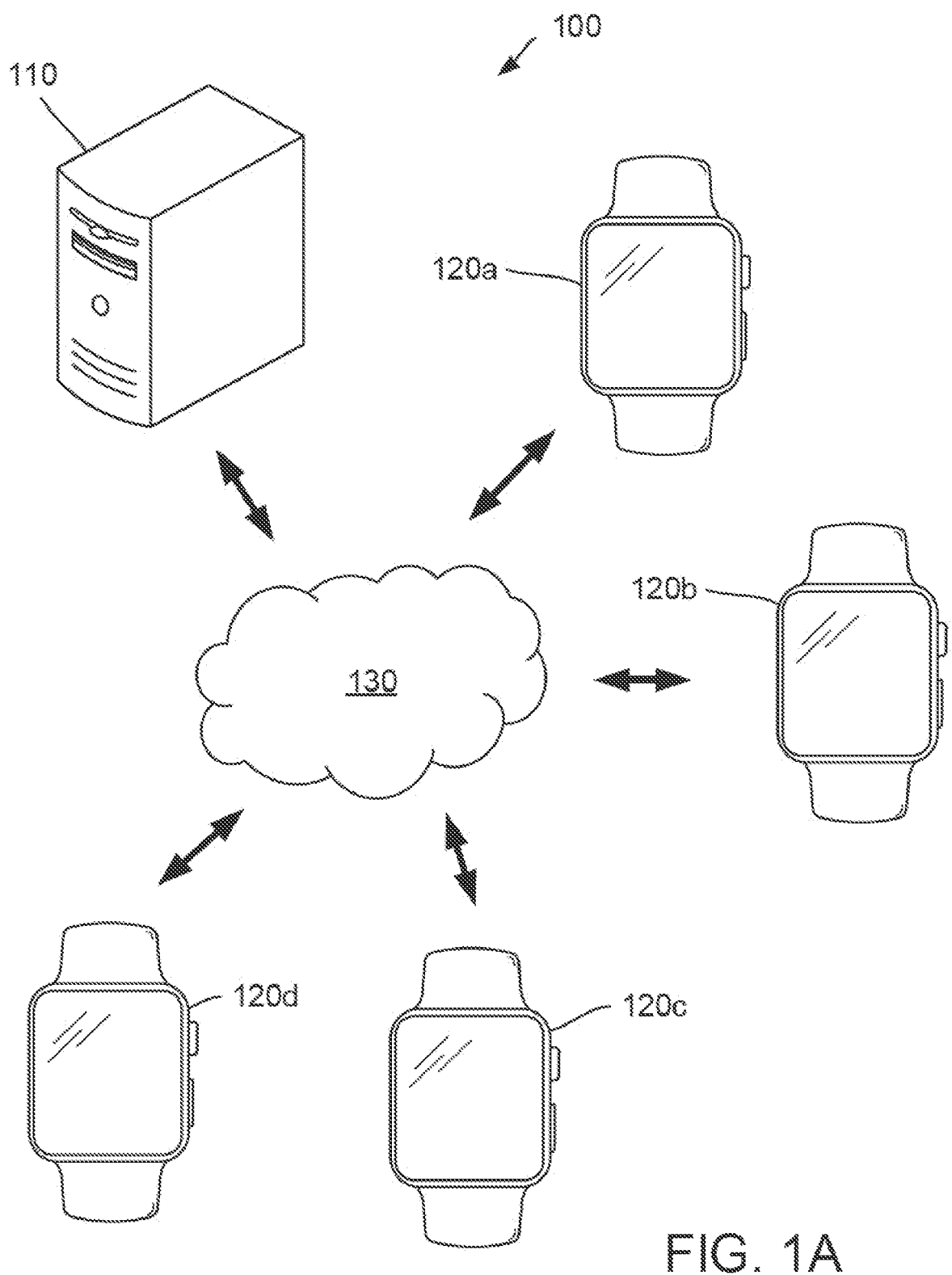
FIG. 1A is a diagram of an example system for assisting users in performing medical procedures.

When treating a patient in cardiac arrest, caretakers often follow guidelines for decision making and timing of interventions to improve the likelihood of success. In many cases, hospitals mandate that providers be trained in these life-saving protocols. Training can include, for example, classroom instruction and simulated scenarios.

However, real-life situations often do not resemble training scenarios. For example, during a training exercise, a complete team of caretakers is often present at the same time. Further, each member of the team is often pre-assigned a particular role within the team, and is already aware of the tasks that he needs to perform. Further still, there are often no extraneous personnel, alarms, or other barriers to effective communication between the team members.

In contrast, in a real-life situation, a patient's room is often filled with care providers, nurses, administrators, and students. If clear roles are not quickly established and a team leader does not assert him or herself, communication and treatment are often compromised. Further, team leaders are not always experienced in treating cardiac arrest. For example, in many cases, a team leader may be a physician who is generally relatively inexperienced in providing care (e.g., a first-year resident physician). Thus, the team leader may not be well versed in the proper treatment procedures.

Further, despite training, caretakers may suffer from information decay that can negatively impact their effectiveness in treating patients. For example, caretakers might undergo periodic training regarding the proper procedures in providing care. However, between training sessions, the caretakers may forget or misremember the procedures, particularly if a lengthy period of time has passed since the last training session. As a result, the caretakers' quality of treatment may suffer.

Further, in many cases, the use of technology is often poorly integrated into these scenarios. For example, medications given and procedures performed are often recorded on pen and paper by physicians and nurses, and immediate electronic decision-making support is often unavailable. As another example, time is often kept by an individual whose voice may be drowned out by other voices and noises in the room. Thus, after a medical intervention has concluded, there may be multiple—sometimes inaccurate—records of when interventions occurred, which affects the quality of debriefings.

To improve the likelihood of success, caretakers can use an electronic system for coordinate their efforts when treating a patient in cardiac arrest. The electronic system can provide each user with a clear indication of his role in an intervention team, provide information regarding what tasks to perform and when to perform those tasks, and provide feedback regarding the effectiveness of his performance. Further still, the electronic system can provide information to caretakers when treating a patient, without requiring that the caretakers hold a device, book, or other object while doing so. Thus, the electronic system allows caretakers to treat the patient more effectively, and while having full use of their hands.

Further, the electronic system can provide team management information to one or more users (e.g., a team leader), such that important information regarding the patient's care and the efforts of the users is readily accessible to an overseer. For example, the electronic system may help administrators assess the user's compliance with established treatment protocols, and to evaluate the performance of one or more users during and after their efforts in treating a patient. Further still, the electronic system can accurately record information regarding the patient's care, including the patient's vital signs, the tasks that were performed in treating the patient, and the time at which those tasks were performed. Thus, accurate records of the treatment can be subsequently reviewed during debriefings or other retrospective applications. Further still, the electronic system can be used as an education tool to instruct users in proper treatment techniques and protocols.

An example electronic system 100 is shown in FIG. 1A. The electronic system 100 includes a computing device 110 and several wearable computing devices 120a-d. The computing device 110 and the wearable computing devices 120a-d are communicatively coupled via a network 130.

Figure 1B:
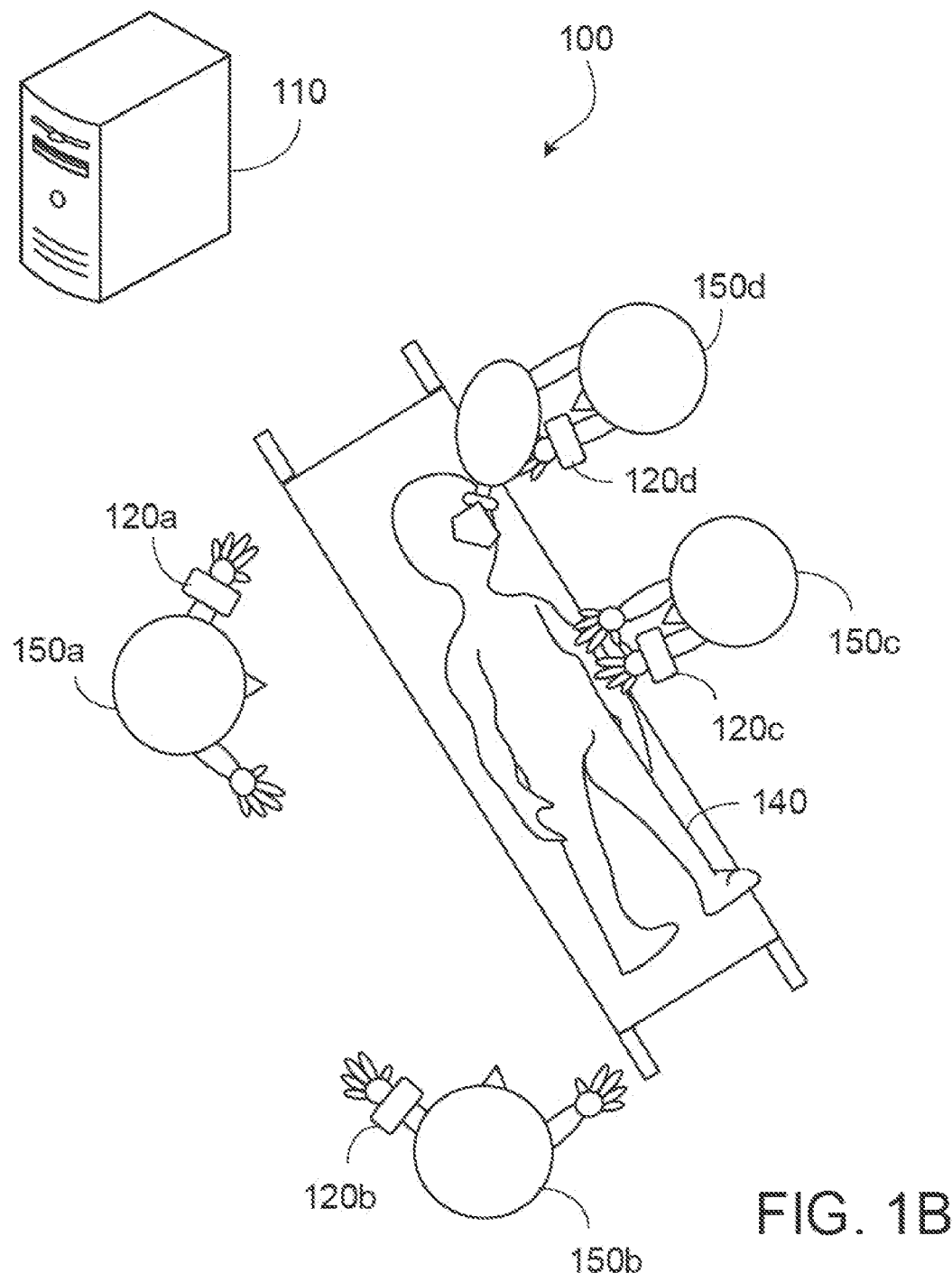
FIG. 1B is a diagram of an example environment for utilizing the system shown in FIG. 1A.

An example environment for utilizing the electronic system 100 is shown in FIG. 1B. In this example, a patient 140 is in cardiac arrest and is being treated by four members 150a-d of a medical intervention team. Each of the members 150a-d is assigned a particular role in treating the patient. The member 150a is assigned a leadership role, and is tasked with coordinating and managing the efforts of the other members of the team in treating the patient. The member 150b is assigned the recorder role, and is tasked with recording the tasks that were performed during the course of treating the patient. The member 150c is assigned a rescuer role, and is tasked with performing cardiopulmonary resuscitation (CPR) (e.g., applying chest compressions to the patient) during the course of treatment. The member 150d is assigned a respiration monitoring role, and is tasked with monitoring the respiration of the patient during the course of treatment and administrating breaths as necessary. Although example roles are described above, this is merely an illustrative example. In practice, other roles are also possible, either instead of in addition to those described above.

Each member 150a-d wears a respective wearable computing devices 120a-d. Each wearable computing device 120a-d is programmed to assist its wearer in performing his duties as a part of the intervention team.

For instance, the wearable computing device 120a can be programmed to assist the member 150a in performing his duties as a leader of the team. For example, the wearable computing device 120a can collect information from each of the other wearable computing devices 120b-d, and present the information to the member 150a to assist him in managing the effort of the intervention team. The wearable computing device 120a can also transmit to each of the other wearable computing devices 120b-d to assist the member 150a in directing efforts of each member of the team. The wearable computing device 120a can also receive information from the computing device 110 (e.g., information regarding the patient, such as patient records, or information regarding potential treatment protocols that can be used to treat the patient). The wearable computing device 120d can also transmit information to the computing device 110 (e.g., information regarding the actions taken by the member 150a, and information received from each of the other wearable computing devices 120d).

The wearable computing device 120b can be programmed to assist the member 150b in performing his duties as the recorder for the team. For example, the wearable computing device 120b can present the member 150b with a series of tasks that can be potentially performed by the members of the team, and allow the member 150b to specify which of those specific tasks that have been performed. The wearable computing device 120b can also record information regarding the performance of those tasks (e.g., the time at which the task was performed, performance parameters associated with those tasks, and so forth). Performance parameters can include, for example, details regarding how a particular task was performed. As an example, if a defibrillation was performed, a performance parameter can include the amount of energy that was applied in performing the defibrillation. As another example, if a drug was administered, performance parameters can include the type of drug administered, the amount of drug administered, the rate at which it was administered, and/or other information pertaining to the administration of the drug. This information can in some cases, be recorded automatically by the wearable computing device 120b, or in some cases, manually entered by its wearer. The wearable computing device 120b can also transmit this information to the wearable computing device 120a (e.g., to provide the member 150a with information to assist him in making decisions on behalf of the team) and/or the computing device 110 (e.g., to record the information to future retrieval and review). In some cases, information obtained by the wearable computing device 120b can be used to modify the behavior of other devices of the electronic system 100 (e.g., resetting countdown timers and/or displaying alerts on one or more of the other devices).

The wearable computing device 120c can be programmed to assist the member 150c in performing his duties as the rescuer for the team. For example, the wearable computing device 120c can present the member 150c with instructions from the member 150a, instruct the member 150c to determine a particular action with respect to the patient (e.g., applying chest compressions to the patient). The wearable computing device 120b can also obtain sensor data, and based on that sensor data, determine information regarding the efforts of member 150c. For example, the wearable computing device 120c can acquire sensor information from pressure sensors, chest displacement sensors, and/or motion sensors, and determine the length of time that the member 150c has been performing chest compression, the rate at which the member 150c is preforming chest compressions, and the pressure or force being applied to the patient by those chest compressions. The wearable computing device 120c can also present that information to the member 150c, such that the member 150c can adjust this performance accordingly. The wearable computing device 120c can also transmit this information to the wearable computing device 120a (e.g., to provide the member 150a with information to assist him in making decisions on behalf of the team) and/or the computing device 110 (e.g., to record the information to future retrieval and review).

The wearable computing device 120d can be programmed to assist the member 150d in monitoring the respiration of the patient during the course of treatment. For example, the wearable computing device 120d can also obtain sensor data, and based on that sensor data, determine information regarding the respiration of the patient 140. For example, the wearable computing device 120d can acquire sensor information from oxygen sensors, carbon dioxide sensors, perfusion sensors, and/or other sensors, and determine information regarding the respiration and perfusion of the patient. The wearable computing device 120d can also present that information to the member 150d, such that the member 150d can adjust this performance accordingly (e.g., by increasing the delivery of oxygen to the patient). The wearable computing device 120d can also transmit this information to the wearable computing device 120a (e.g., to provide the member 150a with information to assist him in making decisions on behalf of the team) and/or the computing device 110 (e.g., to record the information to future retrieval and review).

The functionality of each of the components of the system 100 is described in greater detail below.

In general, the computing device 110 can be any electronic device that processes, transmits, and receives data. The computing device 110 stores information relating to the patient's treatment. For example, the computing device 110 can store information regarding the performance of particular tasks during the patient's treatment and the time in which those tasks were performed. In some cases, the computing device 110 can also manage communications between the wearable computing devices 120a-d. For example, in some cases, the computing device 110 can receive information from one or more of the wearable computing devices 120a-d, and transmit some or all of that information to one or more of the other wearable computing devices 120a-d. In some cases, the computing device 110 can also transmit information collected from each of the wearable computing devices 120a-d to other devices for recordation (e.g., by exporting the information or a summary of the information to an electronic medical records system). Examples of the computing device 110 include computers (such as desktop computers, notebook computers, server systems, embedded devices, etc.), mobile computing devices (such as cellular phones, smartphones, tablets, personal data assistants, notebook computers with networking capability), and other computing devices capable of transmitting and receiving data from network 130. In some cases, the computing device 110 can be remote from the wearable computing devices 120a-d. For example, in some cases, the computing device 110 can be one or more server computers located in a different room, building, or a geographical region than those of the wearable computing devices 120a-d. The computing device 110 can include devices that operate using one or more operating system (e.g., Microsoft Windows, Apple OSX, Linux, Unix, Android, Apple iOS, Apple watchOS, etc.) and/or architectures (e.g., x86, PowerPC, ARM, etc.)

The wearable computing devices 120a-d can be any electronic device that can be worn on a user's body that processes, transmits, and receives data. Examples of the wearable computing devices 120a-d include devices that can be worn on a user's wrist (e.g., a "smart watch"), devices that can be worn over a user's eye (e.g., "smart glasses"), or devices that can be worn on other parts of a body's body (e.g., hands, arms, head, and so forth). The wearable computing devices 120a-d can each contain one or more electronic control modules (e.g., combinations of circuitry, firmware, and/or software) that allow each wearable computing device 120a-d to receive, interpret, process, and transmit information. The wearable computing devices 120a-d can include devices that operate using one or more operating system (e.g., Microsoft Windows, Apple OSX, Linux, Unix, Android, Apple iOS, Apple watchOS, etc.) and/or architectures (e.g., x86, PowerPC, ARM, etc.)

In some cases, wearable computing devices 120a-d present information to its wearer (e.g., through a screen or other display device), and allow the wearer to input selections, commands, or other inputs (e.g., through a touch sensitive surface, buttons, dials, knobs, levels, switches, and so forth). In some cases, a wearable computing device 120a-d can include a touch sensitive screen that both displays information to a wearer and allows the user to input information into the wearable computing device 120a-d by touching the screen. In some cases, a wearable computing device can include a microphone that allows the user to input information by speaking words or phrases.

In some cases, the wearable computing devices 120a-d can communicate with other computing devices 120a-d and/or the computing device 110 directly (e.g., directly over a communications network). In some cases, the wearable computing devices 120a-d can communicate with other computing devices 120a-d and/or the computing device 110 indirectly. As an example, one or more of the wearable computing devices 120a-d can be "paired" to a respective mobile device (e.g., via a Bluetooth connection, near field communication (NFC) connection, or some other network connection to a cellular phone, a smart phone, a tablet, or some other mobile device). That mobile device can then communicate with another wearable computing device 120a-d, either directly with that wearable computing device 120a-d, or indirectly through another mobile device "paired" to that wearable computing device 120a-d. Similarly, one or more of the wearable computing devices 120a-d can be "paired" to one or more separate and discrete sensors (e.g., via a Bluetooth connection, near field communication (NFC) connection, or some other network connection to one or more sensors).

Network 130 can be any communications network through which data can be transferred and shared. For example, network 130 can be a local area network (LAN) or a wide-area network (WAN), such as the Internet. Network 130 can be implemented using various networking interfaces, for instance wireless networking interfaces (such as WiFi, Bluetooth, or infrared) or wired networking interfaces (such as Ethernet or serial connection). Network 130 also can include combinations of more than one network, and can be implemented using one or more networking interfaces.

As described above, the wearable computing device 120a can be programmed to assist a user assigned to the leader role (i.e., the e.g., member 150a, also referred to as the "leader"). For example, in some cases, the wearable computing device 120a can receive patient information from the computer device 110 or another external system (e.g., a patient intake system, a hospital notification system, an emergency code notification system, or an electronic medical records system). Based on this information, the wearable computing device 120a can notify the leader that a patient is in cardiac arrest, the location of that patient (e.g., a particular room or area of a hospital), and/or the time at which the cardiac arrest began.

The wearable computing device 120a also allows the leader to initiate a medical intervention on behalf of the patient. For example, as shown in FIG. 2A, the wearable computing device 120a can include a graphical user interface (GUI) 200 that presents the leader with an option to initiate a medical intervention (often referred to as initiating a "code"). When the leader selects this option (e.g., by touching an icon on a screen of the device or by giving an audible command to the device), the wearable computing device 120a records the time at which the selection was made (e.g., by recording a timestamp), and transmits this information to the computing device 110 for storage. The wearable computing device 120a and/or the computing device 110 can also transmit a notification to one or more of the other wearable computing devices 120b-d to inform their members of the intervention team that their services are needed.

As shown in FIG. 2B, after the leader initiates the intervention, the wearable computing device 120a presents the leader with a list of possible intervention protocols that an intervention team can follow to treat the patient. Information regarding each protocol can be retrieved, for example, from the computing system 110, and/or pre-stored on some of all of the wearable computing devices 120a-d. Each protocol can include, for example, specific tasks to be performed with respect to the patient, particular conditions under which to perform those tasks, and times in which to perform those tasks. Each protocol can also specify, for example, the division of tasks between multiple members of an intervention team. For example, each protocol can specify that particular tasks be performed by particular members of the team, while other tasks be performed by other members of the team. In some cases, each protocol can correspond to a particular medical diagnosis, and the leader can select an appropriate protocol based on his assessment of the patient. When the leader selects a particular protocol, the wearable computing device 120a records the time at which the selection was made (e.g., by recording a timestamp), and transmits this information to the computing device 110 for storage.

Upon selecting a protocol, the wearable computing device 120a presents the leader with one or more prompts to perform tasks in accordance with the selected protocol. For example, the selected protocol may specify that the cardiac rhythm of the patient be measured at a particular time; thus, as shown in FIG. 2C, the wearable computing device 120a can present the leader with a prompt to measure the cardiac rhythm of the patient at the appropriate time. The prompt can include, for example, a visual indication (e.g., an image, text, an animation, a "pop-up," a change in color, or other visual indication), an audible indication (e.g., a sound effect, music, or other audible indication), and/or a haptic indication (e.g., a vibration).

Further, electronic system 100 can prompt other users to perform tasks in accordance with the selected protocol. For example, subsequent to the selection of a particular protocol by the leader, information about the selected protocol can be provided to one or more of the wearable computing devices 120c-d by, for example, the computing device 110 and/or by the wearable computing device 120a. The information provided to the one or more wearable mobile devices can include, e.g., one or more particular tasks for a user perform during the intervention and the time at which such tasks should be performed. For example, a user assigned to the recorder role (e.g., member 150b, also referred to as the "recorder") is wearing the wearable computing device 120b (programmed to assist those assigned to the recorder role); thus, the wearable computing device 120b can present the recorder with a prompt to perform a particular task at the appropriate time. Similarly, a user assigned to the rescuer role (e.g., member 150c, also referred to as the "rescuer") is wearing the computing device 120c (programmed to assist those assigned to the rescuer role); thus, the wearable computing device 120c can present the rescuer with a prompt to perform a particular task assigned to the recorder at the appropriate time. Likewise, a user assigned to the respiration monitoring role (e.g., the ember 120d, or the "respiration monitor") is wearing the computing device 120d (programmed to assist those assigned to the respiration monitoring role); thus, the wearable computing device 120d can present the respiration monitor with a prompt to perform a particular task assigned to the recorder at the appropriate time.

Figure 2E:
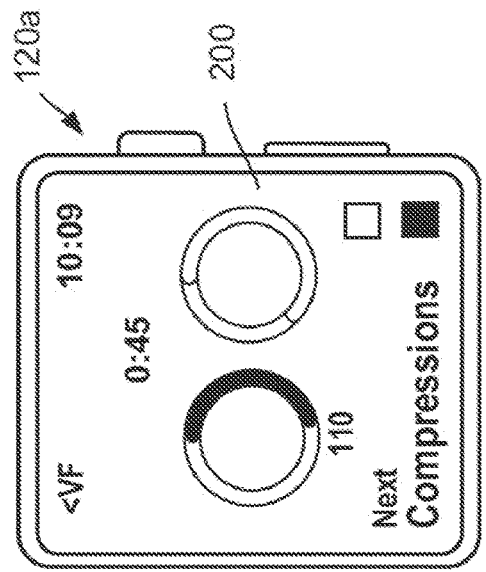
Figure 2G:
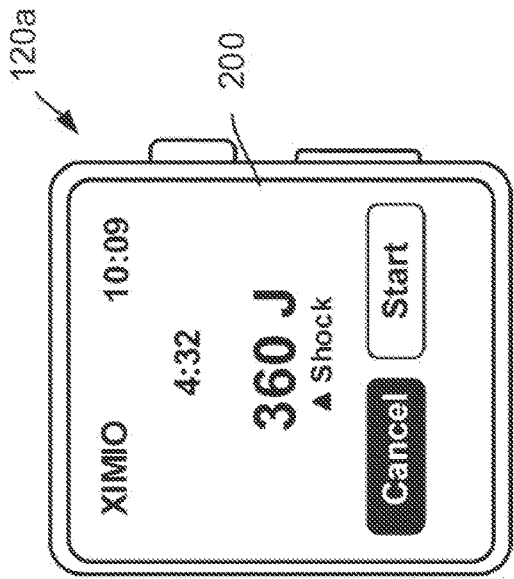
Figure 2D:
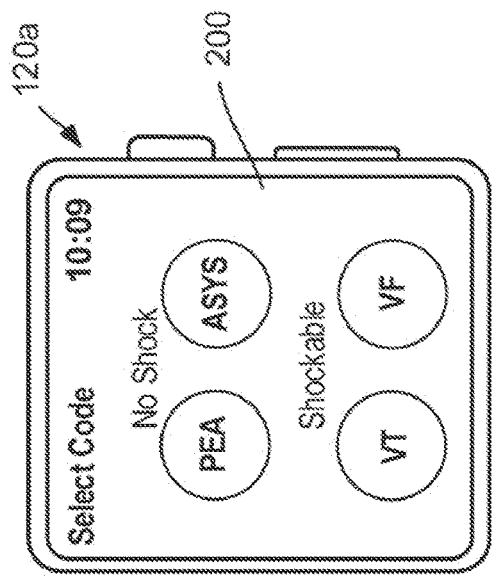

In some cases, the selected protocol may specify different courses of treatment depending on the condition of the patient at a particular time. In some cases, information regarding the condition of the patient can be determined based on the assessment by the leader. For example, as shown in FIG. 2D, the wearable computing device 120a can present the member 150a with several different diagnostic choices, each corresponding to a different possible condition of the patient. The leader can select an appropriate diagnosis based on his assessment of the patient. When the leader selects a particular diagnosis, the wearable computing device 120a records the time at which the selection was made (e.g., by recording a timestamp), and transmits this information to the computing device 110 for storage.

In some cases, a wearable computing device can alert a user that a particular task should be taken in the future, such that the user is prepared to perform that task at the appropriate time. For example, when the member 150a selects the "VF" diagnosis shown in FIG. 2D (corresponding to a diagnosis of ventricular fibrillation), in response, the wearable computing device 120a can present information to the member 150a regarding a protocol to be performed based on that diagnosis. For instance, the protocol may specify that the leader defibrillate a patient at a particular time; as shown in FIG. 2E, the wearable computing device 120a can present a timer 202 that counts down (e.g., via a numerical countdown and/or an animated progress bar or arc), indicating when the defibrillation should be performed.

Figure 2F:
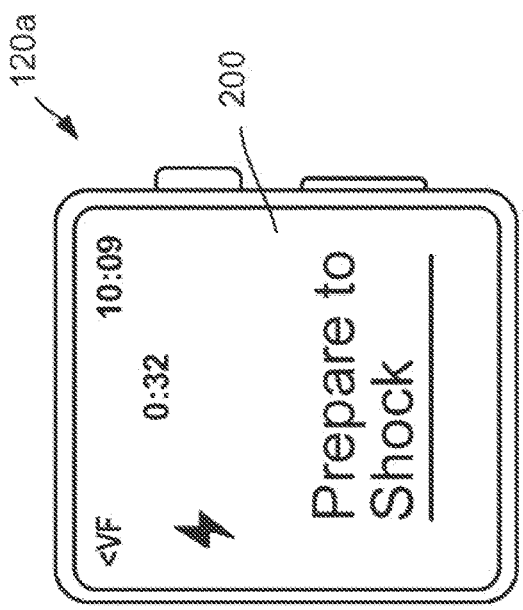

As shown in FIG. 2F, when the countdown is complete, the wearable computing device 120a presents an alert to the member 150a that defibrillation should be performed at that time. As shown in FIG. 2G, the wearable computing device 120a can subsequently present information regarding the defibrillation (e.g., the suggested energy that should be applied to the patient), and an option to confirm that the defibrillation was performed (e.g., a "start" button). When the member 150a confirms performance of the defibrillation, the wearable computing device 120a records the time at which the selection was made (e.g., by recording a timestamp) and information regarding the performance of the task (e.g., the energy of the defibrillation), and transmits this information to the computing device 110 for storage. In some cases, this information can be presented by one or more of the other wearable computing devices 120a. For example, in some cases, the wearable computing device 120b can also present an interface (e.g., the interface shown in FIG. 2G) to the member 150b (e.g., the recorder), such that he can also confirm performance of the task. Similarly, upon confirmation, the wearable computing device 120b records the time at which the selection was made and information regarding the performance of the task, and transmits this information to the computing device 110 for storage.

Although example tasks are described above, these are merely illustrative examples. In practice, a protocol can specify other tasks, either instead of or in addition to those described above. Accordingly, the wearable computing device 120a can provide other information to the leader, as appropriate for the particular task. Further, although particular tasks are described as being assigned to the leader, in practice, these tasks can be assigned to other members of the intervention team. Accordingly, the other wearable computing devices 120b-d can provide information to their respective users, as appropriate for the particular task. To illustrate, FIGS. 3A-C show additional example alerts and/or prompts that can be displayed to one or more members of the intervention team in accordance with the selected protocol. FIG. 3A shows an example wearable computing device 120a and GUI 300 displaying an alert to the leader to prepare to clear the patient in preparation for defibrillation. FIG. 3B shows an example wearable computing device 120a and GUI 300 displaying a prompt to the leader to check the patient's pulse. FIG. 3C shows an example wearable computing device 120c and GUI 300 displaying a prompt to the rescuer to resume performing CPR on the patient. In practice, the wearable computing devices can present other alerts, prompts, or information, depending on the implementation.

Figure 4A:
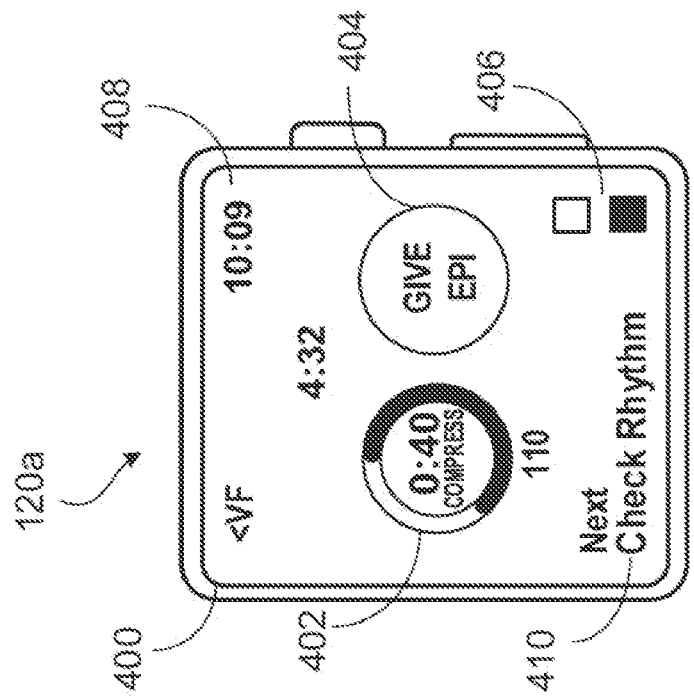
FIGS. 4A-4B are diagrams of example graphical user interfaces presented by a wearable computing device.

In some implementations, the wearable computing device 120a can provide the leader with information that summarizes the patient's condition, the task or tasks currently being performed, and future tasks or tasks to be performed. As an example, as shown in FIG. 4A, the wearable computing device 120a can present a GUI 400 with a CPR portion 402. The CPR portion 402 includes a timer that indicates a recommended amount of time that a rescuer should continuously perform CPR (e.g., according to the selected protocol or general guidelines), and a length of time that the current rescuer has been performing CPR on the patient. When the timer expires, this indicates that a different rescuer should take over performing CPR on the patient. In response, the system 100 can notify another user to perform CPR. For example, in some cases, the wearable computing device 120a can display a notification to the member 150a, reminding the leader to instruct another member of the team to perform CPR. As another example, in some cases, the wearable computing device 120c can display a notification to the rescuer, reminding the rescuer to cease performance of CPR and pass the duties to another member of the team. This can be beneficial, for example, to reduce the likelihood that a rescuer becomes fatigued in performing CPR for too long a period of time. The CPR portion 402 also indicates the compression rate of the CPR. Determination of the compression rate is described in greater detail below.

Figure 4B:
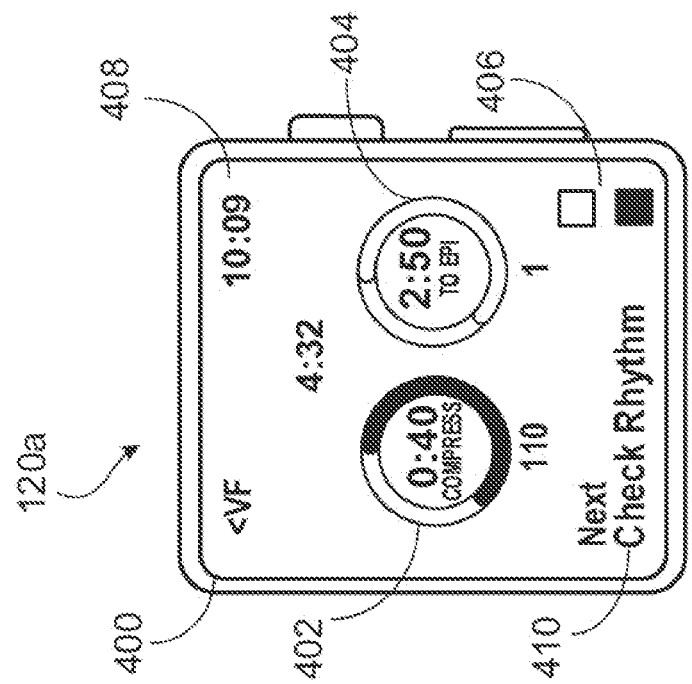

The wearable computing device 120a also presents a GUI 400 having an upcoming task portion 404. The upcoming task portion 404 indicates an upcoming task that is to be performed in accordance with the selected protocol, and a timer that counts down the time at which that task should be performed. As shown in FIG. 4B, when the timer expires, the wearable computing device 120 can provide a prompt in the upcoming task portion 404 to perform the task.

The wearable computing device 120a also presents a GUI 400 having a task preview portion 410. The task preview portion 410 indicates an upcoming task that is to be performed after upcoming task in accordance with the selected protocol (e.g., the task to be performed subsequent to that shown in the upcoming task portion 404).

The wearable computing device 120a also presents a GUI 400 having a treatment status portion 406. The treatment status portion 406 indicates the quality and/or efficacy of the intervention team's treatment of the patient. For example, the treatment status portion 406 can include an indication of a CPR quality index (e.g., a composite index based on factors such as compression rate, compression pressure, pressure decay, compression depth, and/or compression rate variability) and/or a perfusion quality index (e.g., a composite index based on factors such as perfusion pressure, arterial pressure and/or end tidal CO, and/or brain/tissue saturation). These indications can be provided as a numerical score (e.g., on a quality scale of 1-10) and/or as a color score (e.g., on a quality scale of red, orange, yellow, light green, and green, indicating an ascending quality scale from "poor" to "good" quality). The GUI 400 can also include a time portion 408 that indicates the time that has elapsed since the leader initiated the intervention.

Figure 4C:
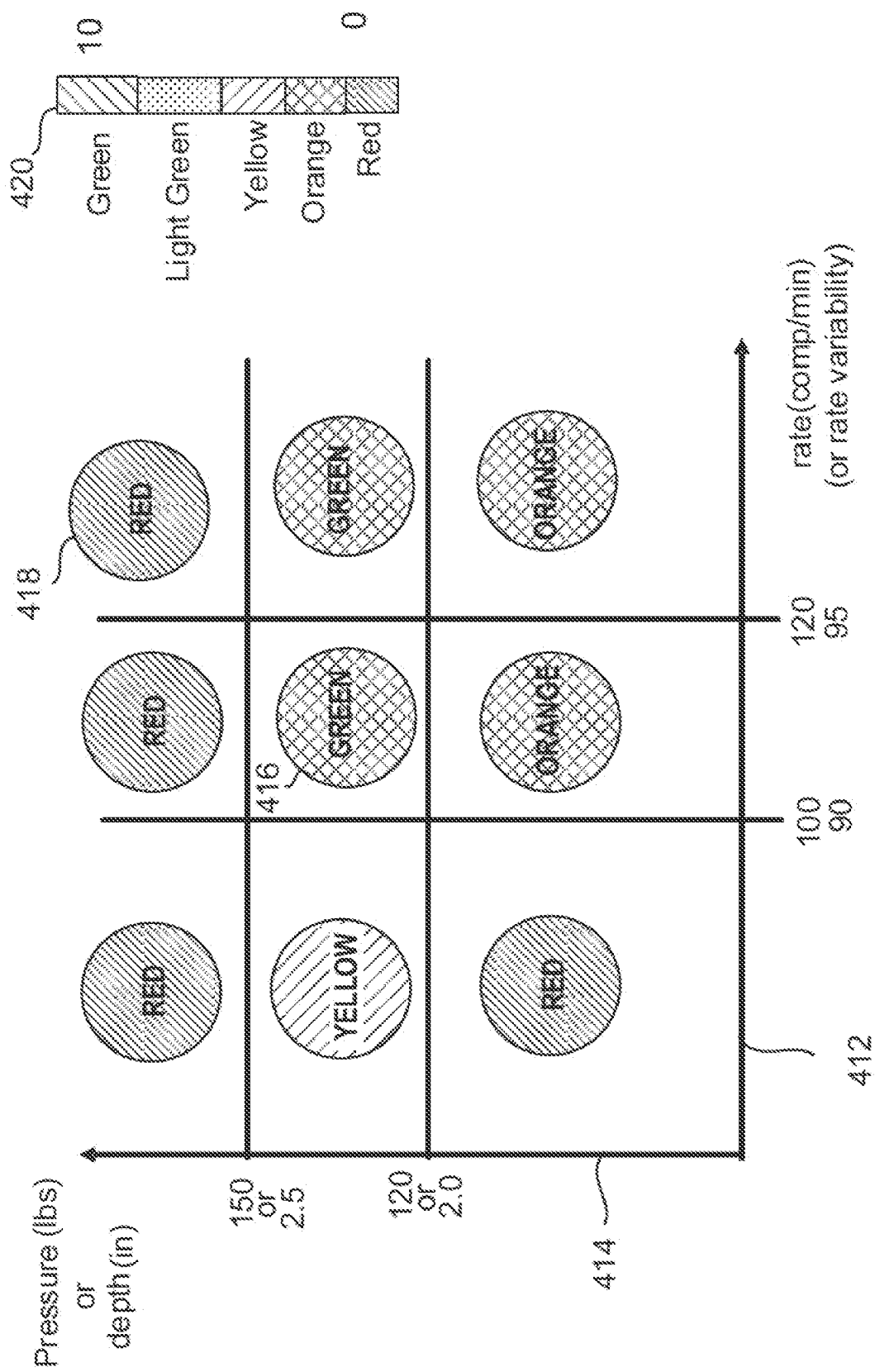
FIG. 4C is an example chart for determining a CPR quality index score.

An example technique for determining a score for the CPR quality index is shown in FIG. 4C. As shown in FIG. 4C, two factors can be considered in determining a CPR quality index score: compression rate (shown on axis 412) and compression pressure (shown on axis 414). Depending on the values of the compression rate and compression pressure, a particular qualitative score can be assigned. For example, when the compression pressure is between 120 and 150 lbs. and the compression rate is between 100 and 120 compressions per minute, the CPR quality index can be assigned a "good" score (e.g., depicted as a green colored icon 416). However, when the compression pressure is greater than 150 lbs. and the compression rate is greater than 120 compressions per minute, the CPR quality index can be assigned a "poor" score (e.g., depicted as a red colored icon 418), indicating that the rescuer is performing compressions in an ineffective or unsafe manner. Further, when the compression pressure is less than 120 lbs. and the compression rate is greater than 100 compressions per minute, the CPR quality index can be assigned a "fair" score (e.g., depicted as a orange colored icon 420), indicating that the rescuer is performing compressions moderately effectively. Likewise, other combinations of values can correspond to different scores for the CPR quality index. Although example ranges for each factor are provided, these are merely illustrative examples. In practice, other ranges are possible, depending on the implementation. Further, although example "color" scores are described, these are merely illustrative examples.

In practice, any number of colors can be used to represent scores (e.g., two colors, three colors, four colors, and so forth). Likewise, numerical scores can be used either instead of, or in combination, with color scores. As an example, as shown in FIG. 4C, a color scale 420 can be used to represent both color scores and numerical scores across a range.

Although two example variables are described above, those are merely illustrative examples. In practice, different variables can be used to determine a score. For example, as shown in FIG. 4C, instead of determining a score based on compression rate, compression depth can be used instead (e.g., as shown on axis 412). As another example, as shown in FIG. 4C, instead of determining a score based on compression rate, compression variability can be used instead (e.g., as shown on axis 412). Compression variability can be, in some cases, the number of deviations from a particular range of compression rates (e.g., an ideal or recommended range of compression rates. Further, although two a two-variable technique for determining a score is described, this is merely an illustrative example. In practice, any number of different variables can be used to determine a score (e.g., a three-variable technique, a four-variable technique, and so forth).

Figure 4D:
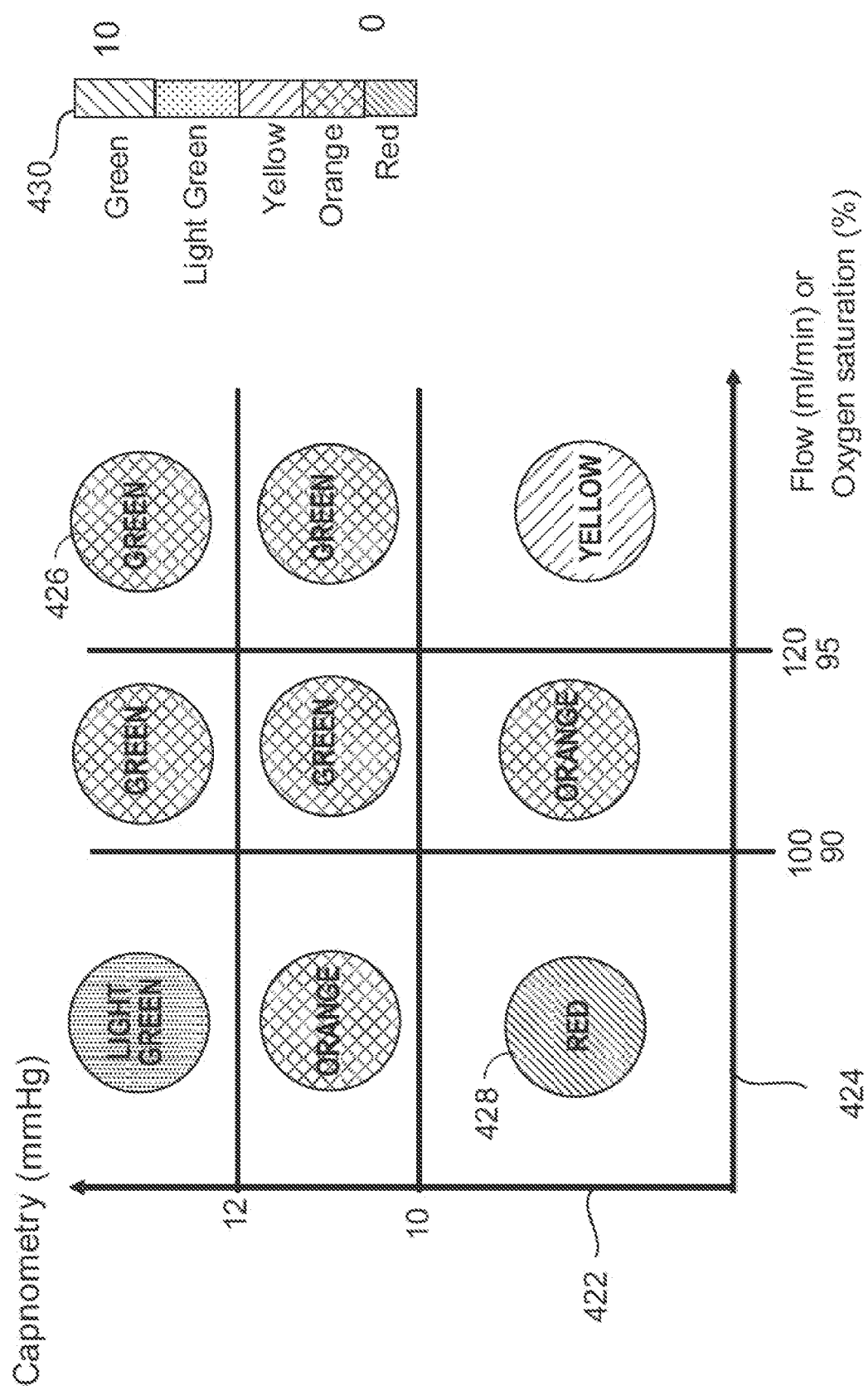
FIG. 4D is an example chart for determining a perfusion quality index score.

This technique can be similarly used to determine score of the perfusion quality index. As an example, a technique for determining a score for the perfusion quality index is shown in FIG. 4D. As shown in FIG. 4D, two factors can be considered in determining a score: carbon dioxide concentration obtained via capnometry (shown on axis 422) and vascular flow rate (shown on axis 424). Depending on the values of the carbon dioxide concentration and vascular flow rate, a particular qualitative score can be assigned. For example, when the carbon dioxide concentration is greater than 12 mmHg and the vascular flow rate is greater than 120 ml/min, the perfusion quality index can be assigned a "good" score (e.g., depicted as a green colored icon 426). However, when the carbon dioxide concentration is less than 10 mmHg and the vascular flow rate is less than 100 ml/min, the perfusion quality index can be assigned a "poor" score (e.g., depicted as a red colored icon 428), indicating that rescue breathes are being administered in an ineffective manner. Likewise, other combinations of values can correspond to different scores for the perfusion quality index. Although example ranges for each factor are provided, these are merely illustrative examples. In practice, other ranges are possible, depending on the implementation. As an example, in some cases, the ranges of vascular flow rate can be determined based on the location at which the vascular flow is being measured. For instance, when the average vascular flow rate in a healthy patient's leg is 284±21 ml/min in the common femoral (CFA), 152±10 mL/min in the superficial femoral (SFA), 72±5 mL/min in the popliteal, and 3±1 mL/min in the dorsalis pedis. Thus, the range of vascular flow rates for each score can be adjusted to account for differences in the measurement site.

Further, although example "color" scores are described, these are merely illustrative examples. In practice, any number of colors can be used to represent scores (e.g., two colors, three colors, four colors, and so forth). Likewise, numerical scores can be used either instead of, or in combination, with color scores. As an example, as shown in FIG. 4D, a color scale 430 can be used to represent both color scores and numerical scores across a range.

Similarly, although two example variables are described above, those are merely illustrative examples. In practice, different variables can be used to determine a score. For example, as shown in FIG. 4D, instead of determining a score based on vascular flow rate, the percentage of oxygen saturation can be used instead (e.g., as shown on axis 424). Further, although two a two-variable technique for determining a score is described, this is merely an illustrative example. In practice, any number of different variables can be used to determine a score (e.g., a three-variable technique, a four-variable technique, and so forth).

In some cases, the scores can be used to determine when a rescuer is not effectively or safely performing his rescue tasks, and in response, prompt one of the members of the intervention team to take corrective action. For instance, in some cases, the system 100 can notify another user to take over the task of performing CPR. As an example, in some cases, the wearable computing device 120a can display a notification to the member 150a, suggesting that the leader instruct another member of the team to perform CPR. As another example, in some cases, the wearable computing device 120c can display a notification to the rescuer, suggesting that the rescuer cease performance of CPR and pass the duties to another member of the team. As another example, in some cases, the wearable computing devices 120a and/or 120c can present information its wearer with instructions for improving his performance (e.g., a prompt to slow down or speed up his compressions, and/or to apply more or less pressure during his compressions).

Figure 4E:
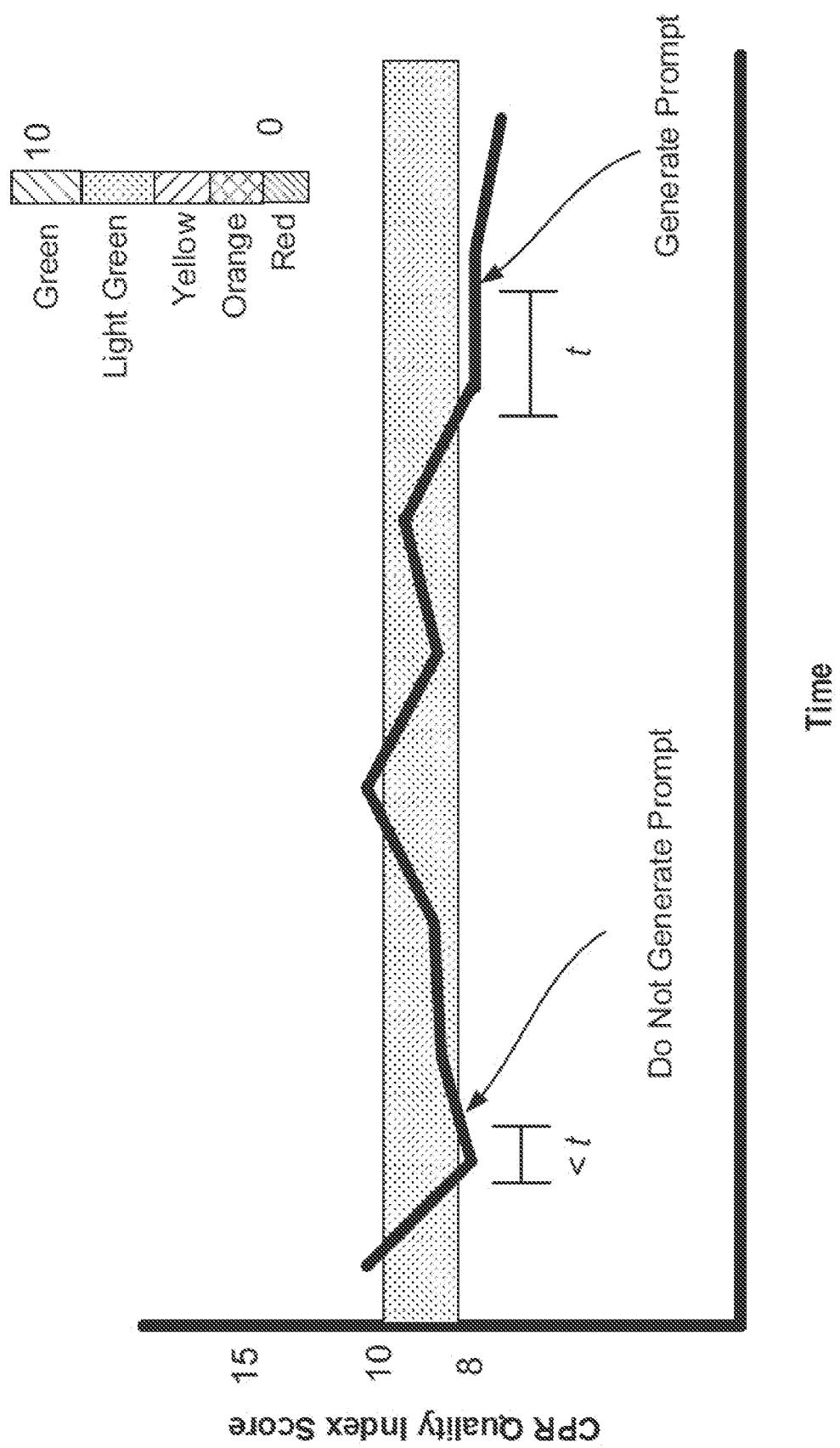
FIG. 4E is an example chart showing the monitoring of the CPR quality index over a period of time.

In some cases, the system 100 can determine that a rescuer is not effectively or safely performing his rescue tasks when a score drops below a threshold level for a particular period of time. For example, as shown in FIG. 4E, the system 100 can record the scores for the CPR quality index over a period of time. If the score drops below a threshold level (e.g., a score of 8) for a threshold length of time t or longer (e.g., 5, seconds, 10 seconds, 15 seconds or some other period of time), the system 100 can determine that a rescuer is not effectively or safely performing his rescue tasks, and in response, prompt one of the members of the intervention team to take corrective action. However, if the score drops below the threshold level for less than the threshold length of time t, the system 100 can continue to monitor the user's performance, but not generate a prompt for corrective action. Although example threshold scores and threshold lengths of time are described, these are merely illustrative examples. In practice, any values can be used. In some cases, the threshold score and the threshold length of time can be defined by a member of the intervention team and/or by a developer of the system 100, and/or defined based on one or more clinical protocols. Similarly, the system 100 can record the scores for the perfusion quality index over a period of time and generate prompts for corrective action when the rescuer is not effectively or safely performing his rescue tasks.

As described above, a user assigned to the recorder role (e.g., member 150d, also referred to as a "recorder") can wear the wearable computing device 120b (corresponding to the recorder role) to assist him in with recording the tasks that were performed during the course of treating the patient. The recorder can be, for example, a user in charge of monitoring medication administration, the use of the defibrillator, and keeping an accurate time of the events.

In an example scenario, the leader has selected a protocol using the wearable computing device 120a, and the wearable computing devices 120a-d present information to the members of intervention team regarding tasks to be performed in accordance with the selected protocol. The wearable computing device 120b allows the recorder to record information regarding which tasks were performed by one of the team members, and at what time those tasks were performed to create an accurate record of the patient's treatment.

Figure 5A:
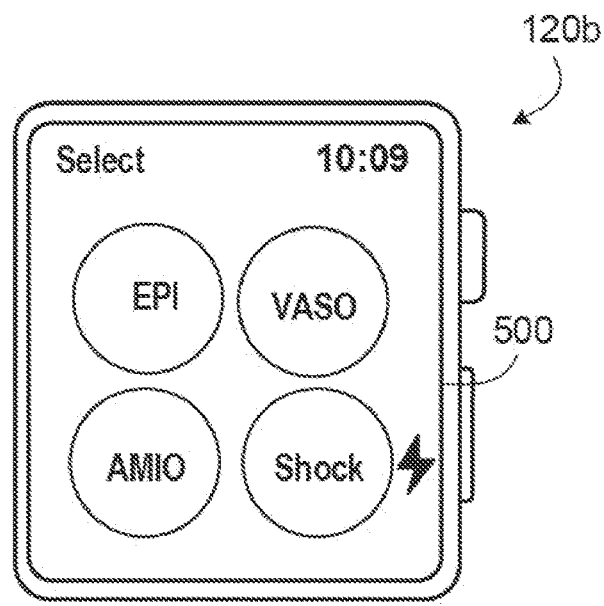
FIGS. 5A-5C are diagrams of example graphical user interfaces presented by a wearable computing device.

For example, as shown in FIG. 5A, the wearable computing device 120b can present a GUI 500 that displays a list of tasks that may be performed by one or more members of the intervention team. This list of tasks can be contextually filtered, such that the user is presented with only a subset of all possible tasks. For example, if the selected protocol specifies that a particular series of tasks be performed, the wearable computing device 120b can present only the most imminent tasks (e.g., the next N tasks) and/or the most recently scheduled tasks (e.g., the last M scheduled tasks), while not presenting other tasks. When the recorder determines that a particular task has been performed (e.g., by observation the performance of that task by one of the members of the intervention team), the user selects that task from the GUI 500. For instance, the recorder may observe than epinephrine has been administered to the patient, and selects the "EPI" option on the GUI 500.

Figure 5B:
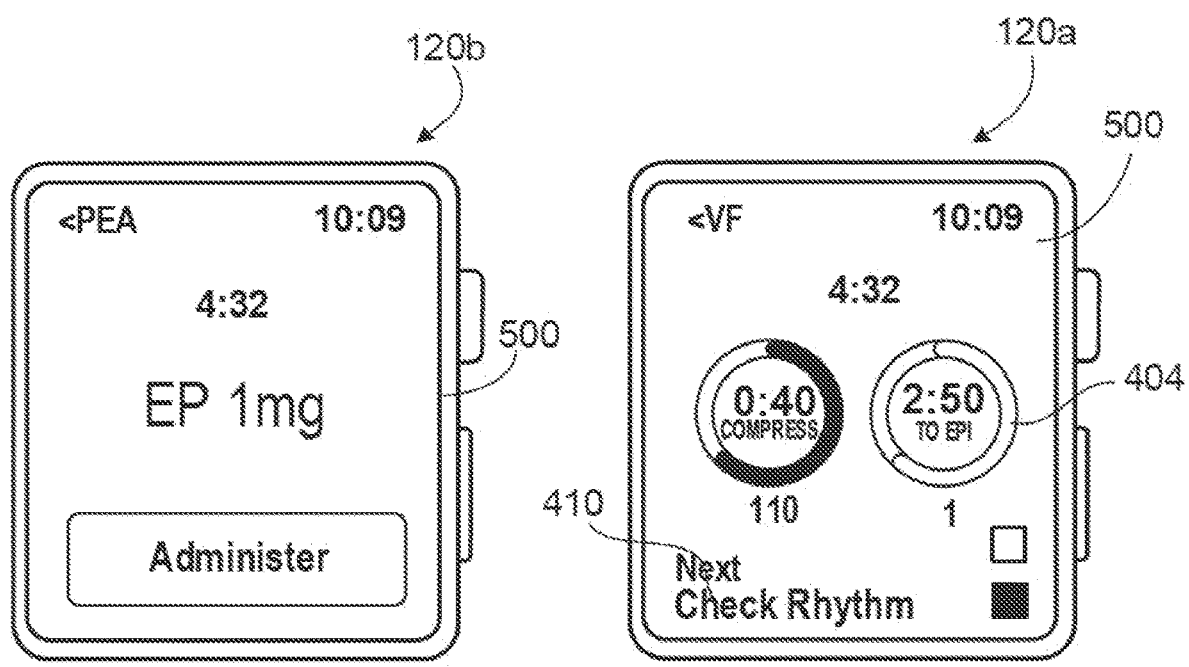

As shown in FIG. 5B, in response, the GUI 500 requests that the recorder confirm the selection (e.g., by selecting the "administer" option). Upon confirmation, the wearable computing device 120b records the time at which the task was confirmed (e.g., by recording a timestamp), and transmits this information to the computing device 110 for storage. The wearable computing device 120b and/or the computing device 110 can also transmit this information to one or more of the other wearable computing devices 120a, 120c, and 120d. For instance, the wearable computing device 120b and/or the computing device 110 can transmit the time at which the administration of epinephrine was confirmed to the wearable computing device 120a. In response, the computing device 120a can update its GUI 400 to reflect the selection, for example by updating the upcoming task portion 404 of the GUI 400 to indicate when the next task (e.g., the task after the administration of epinephrine) should be performed. The computing device 120a can also update the task preview portion 410 of the GUI 400 to indicate the subsequent tasks that should be performed (e.g., tasks to be performed after the task shown in the upcoming task portion 404.

Figure 5C:
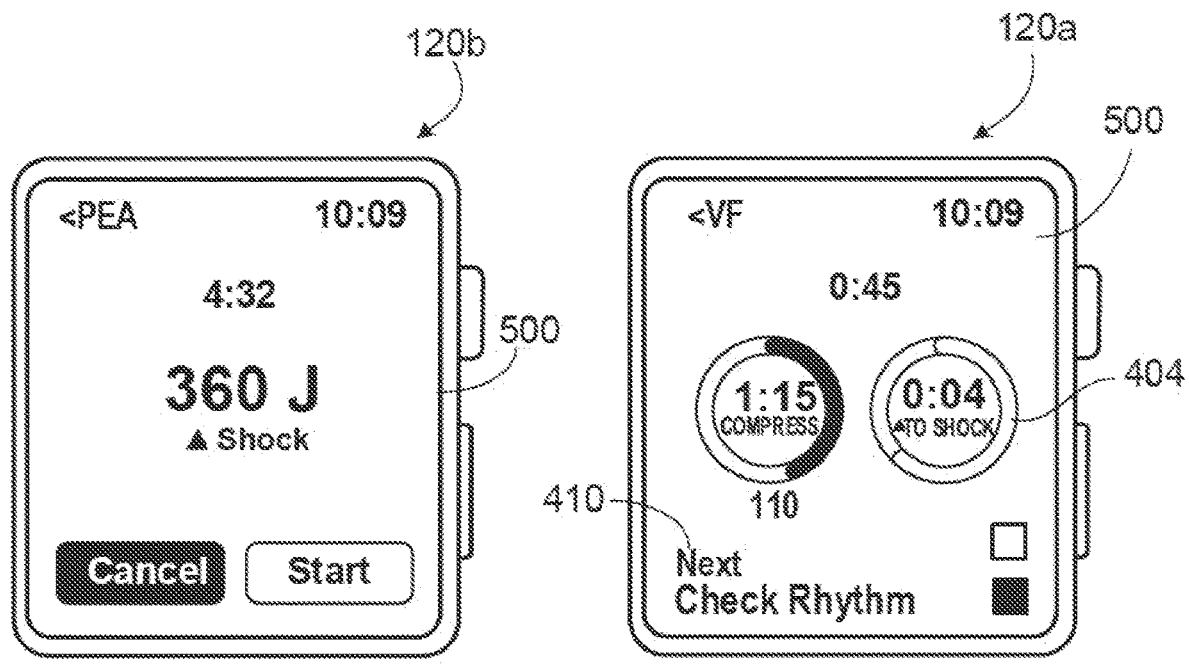

As another example, the recorder may observe than a defibrillation procedure has been performed on the patient, and selects the "Shock" option on the GUI 500. As shown in FIG. 5C, in response, the GUI 500 is updated to request that the recorder confirm the selection (e.g., by selecting the "Start" option). Upon confirmation, the wearable computing device 120b records the time at which the task was confirmed (e.g., by recording a timestamp), and transmits this information to the computing device 110 for storage. As above, the wearable computing device 120b and/or the computing device 110 can also transmit this information to one or more of the other wearable computing devices 120a, 120c, and 120d. For instance, the wearable computing device 120b and/or the computing device 110 can transmit the time at which the performance of defibrillation was confirmed to the wearable computing device 120a. In response, the computing device 120a can update its GUI 400 to reflect the selection, for example by updating the upcoming task portion 402 of the GUI 400 to indicate when the next task (i.e., the task after defibrillation) should be performed. The computing device 120a can also update the task preview portion 410 of the GUI 400 to indicate the subsequent tasks that should be performed (e.g., tasks to be performed after the task shown in the upcoming task portion 404.

Figure 6:
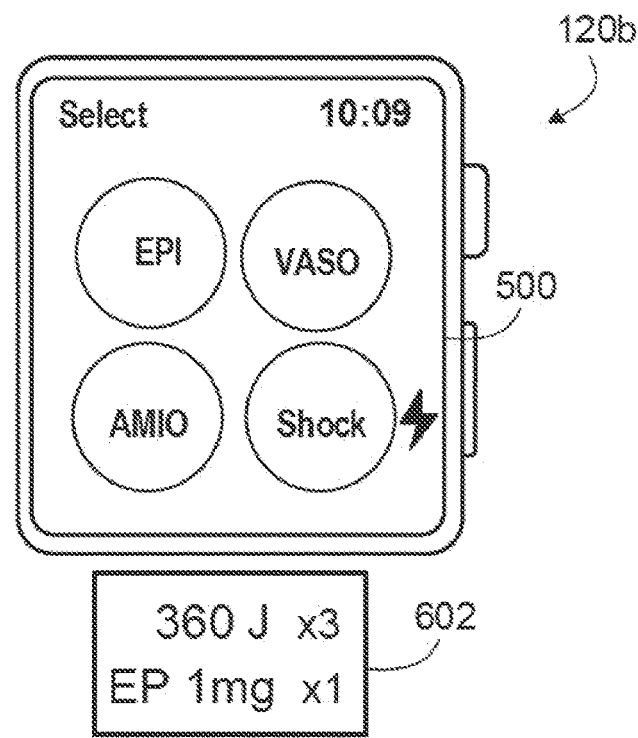
FIG. 6 are diagrams of example graphical user interfaces presented by a wearable computing device.

In the above examples, a GUI presents information on a single screen, such that the user need not scroll through multiple screens of information. However, this need not be the case. In some implementations, a GUI can present information across several screens, and a user can scroll through each of the screens to access additional information. For example, as shown in FIG. 6, the GUI 500 of the wearable computing device 120b can display a list of tasks that may be performed by one or more members of the intervention team. However, the recorder can scroll downwards to access a lower portion 602. This lower portion 602 can present, for example, information regarding past defibrillation procedures that have been performed on the patient (e.g., the number of times that the patient had been previously defibrillated and the amount of energy that was applied), and information regarding past administrations of epinephrine (e.g., the number of times that epinephrine had been previously administered and the dosages). This can be useful, for example, as it allows the recorder to access recordation options corresponding to several different tasks, while also allowing him to access additional information regarding previously performed tasks (e.g., so that he can relay that information to others on the intervention team).

As described above, a user assigned to the rescuer role (i.e., the "rescuer") can wear the wearable computing device 120c (corresponding to the rescuer role) to assist him in performing CPR on the patient.

The wearable computing device 120c can obtain information regarding the effectiveness of the rescuer's efforts in performing CPR on the patient. As an example, referring to FIG. 7, the wearable computing device 120c can present a GUI 700 that presents information regarding the compression pressure of the rescuer's chest compressions, the depth of the compressions, and the compression rate of the rescuer's chest compressions. This allows the rescuer to determine whether he is applying the appropriate amount of pressure to the patient, whether his compressions are appropriately deep, and whether he is applying compressions at the correct rate.

The wearable computing device 120c can also instruct the user regarding the correct compression pressure and/or compression rate, and notify him if he is deviating from the correct procedure. For example, the GUI 700 can include a pressure gauge 702 that indicates whether the rescue is applying a proper amount of pressure (e.g., with a color-coded "good" indication), or whether he is applying an improper amount of pressure (e.g., with color-coded "low" or "heavy" indications). Although example labels are shown, it is understood that these are merely illustrative examples. Other labels can be used, depending on the implementation.

As another example, the GUI 700 can include a compression timer 704 that that indicates the period of time that the rescuer is tasked with performing chest compressions, the rate at which the rescuer is applying those compressions, and whether the rescuer is applying those compressions at the proper rate. For example, the compression timer 704 can include a numerical indicator that indicates the rate (e.g., compressions per minute) of the rescuer's compressions. The compression timer 704 can also include a ring representing the interval of time that the rescuer is tasked with performing chest compressions. For example, when the rescuer is initially tasked with performing chest compressions, the arc can be displayed as a full circle. As time passes, the arc gradually decreases in length. When the arc disappears, this indicates that the rescuer is to discontinue compressions. For example, a second rescuer can be notified to perform CPR. This is beneficial, as it allows the rescuer to quickly determine whether he is applying chest compressions for the appropriate amount of time, and whether he should discontinue chest compressions (and allow another member of the team to take over) to mitigate the effects of fatigue. The interval of time can vary, depending in on the implementation. For example, in some cases, the interval of time can be approximately 1 minute, 2 minutes, three minutes, or another interval of time.

In some cases, the arc can be color-coded to indicate the quality of the rescuer's efforts. For instance, in some cases, the arc can be color-coded to indicate whether the rate of compressions is too fast or too slow. For example, when the rescuer is performing chest compressions too quickly or slowly, the arc can be colored red. When the rescuer is performing chest compressions at the proper rate, the arc can be colored green.

In some cases, the pressure rate indicator 704 can also indicate whether the rate of compressions is relatively constant, or whether the rate of compressions has become inconsistent or uneven. In response, the pressure rate indicator 704 can indicate the uniformly of the chest compression (e.g., through the color coded arc). For example, the arc can be colored green if the chest compressions are being performed relatively uniformly, and red if the chest compressions are being performed relatively unevenly. This can be beneficial, for example, as it is often preferable for the rescuer to perform chest compressions at a uniform rate.

Figure 7:
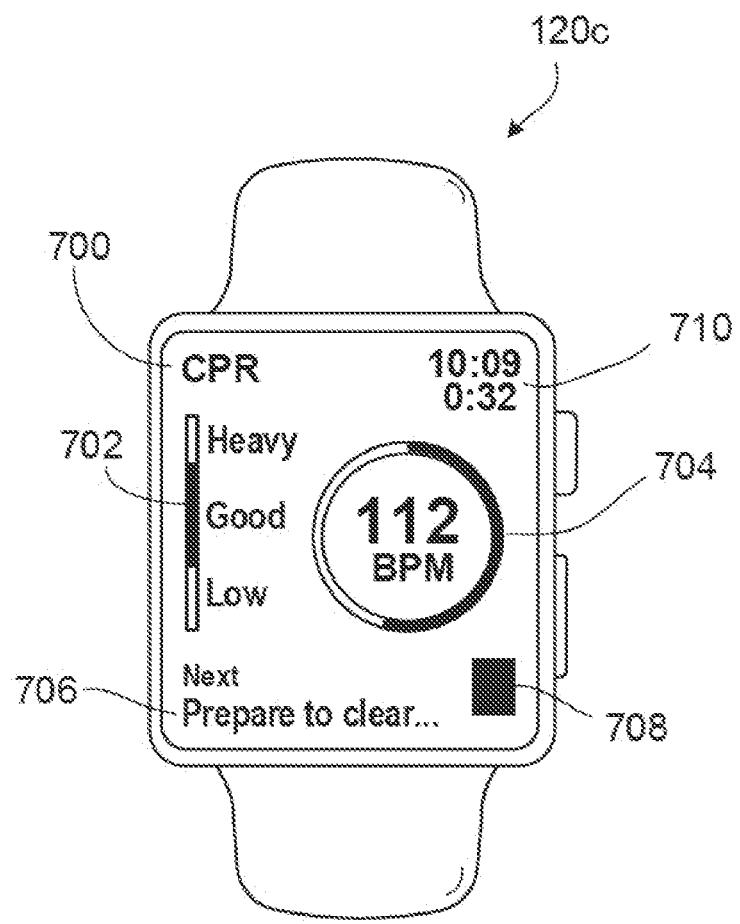
FIG. 7 is a diagram of an example graphical user interface presented by a wearable computing device.

As with the wearable computing device 120a, the wearable computing device 120c can also provide the rescuer with information that summarizes the patient's condition, the task or tasks currently being performed, and future tasks or tasks to be performed. As an example, as shown in FIG. 7, the GUI 700 can include an upcoming task portion 706. The upcoming task portion 706 indicates an upcoming task that is to be performed in accordance with the selected protocol. The wearable computing device 120c also can include a treatment status portion 708. The treatment status portion 708 indicates the quality and/or efficacy of the intervention team's treatment of the patient. For example, the treatment status portion 708 can include an indication of a CPR quality index (e.g., a composite index based on factors such as compression rate, compression pressure, pressure decay, and/or compression rate variability). This indications can be provided as a numerical score (e.g., on a quality scale of 1-10) and/or as a color score (e.g., on a quality scale of red, orange, and green, indicating poor quality, fair quality, and good quality, respectively). The GUI 700 can also include a time portion 710 and indicates the time that has elapsed since the leader initiated the intervention.

Figure 8A:
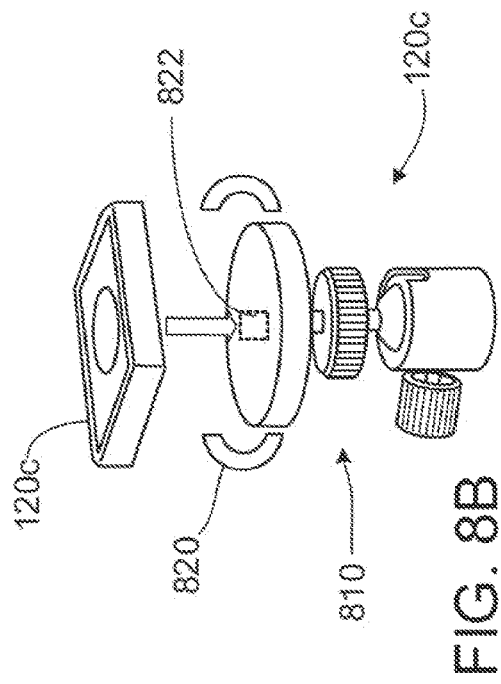
FIG. 8A is diagram of an example wearable computing device mounted on a pad or plate through straps.

The wearable computing device 120c can obtain information regarding the effectiveness of the rescuer's efforts in performing CPR on the patient in various ways. For example, as shown in FIG. 8A, the wearable computing device 120c can be mounted to a pad or plate 802 through straps 804. The straps 804 suspend the wearable computing device 120c above the pad or plate 802, such that a space 806 is defined between the device 120c above the pad or plate 802.

The pad or plate 802 can be constructed from a soft material (e.g., a soft plastic or silicone) to reduce the amount of physical trauma that results from the rescuer's chest compressions. In some cases, the pad or plate 802 can be constructed from a material that is resistant to solvents, such as those used to sanitize materials exposed to biological waste. This can be useful, for example, as it improves the durability of the pad or plate 802 through multiple uses. The pad or plate 802 can be relatively flat (e.g., a disc), or it can be shaped such that it conforms to the exterior surface of a human body.

The pad or plate 802 includes a pressure sensor 808 on an external surface or embedded within it. The pressure sensor 808 detects the amount of pressure that is applied to the pad or plate 802, and transmits this information to the wearable computing device 120c (e.g., through a wired or wireless connection). For example, in some cases, the pressure sensor 808 can include a wireless transmitter (e.g., a Bluetooth radio) that allows the pressure sensor 808 is wirelessly transfer information to an electronic control module within the wearable computing device 120c. Example pressure sensors include, for example, pressure mapping sensors from Tekscan, Inc. (South Boston, MA), such as Tekscan Pressure Mapping Sensors and Tekscan Medical Sensors.

In an example usage of the wearable computing device 120c, the rescuer places the pad or plate 802 on top of the patient's chest, and places his hands in the space 806 (e.g., with interlocking fingers in CPR position). The rescuer then applies compressive pressure to the pad or plate 802, thereby compressing the patient's chest in accordance with a CPR technique. The pad or plate 802 can be beneficial, as it distributes the pressure applied by the rescuer, thereby reducing the likelihood of injury to the patient. As the rescuer performs compressions, the pressure sensor 808 measures the pressure, and transmits the measurements to the wearable computing device 120c. In turn, the wearable computing device 120c presents the information regarding the compressions to the rescuer (e.g., using the GUI 700).

Figure 8B:
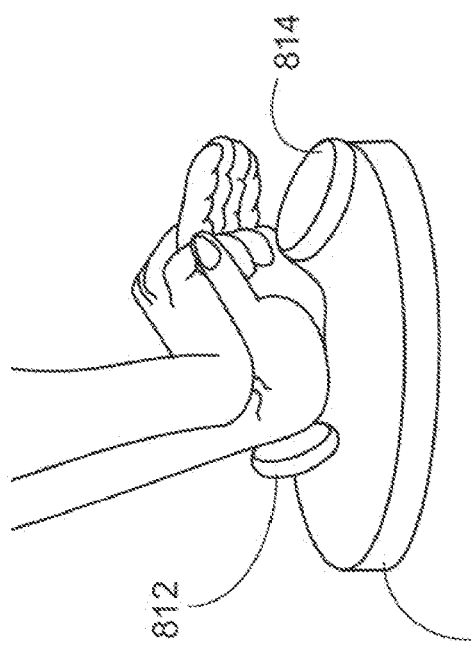
FIG. 8B-8C are diagrams of an example swivel mechanism for mounting the wearable computing device shown in FIG. 8A to the straps.
Figure 8C:
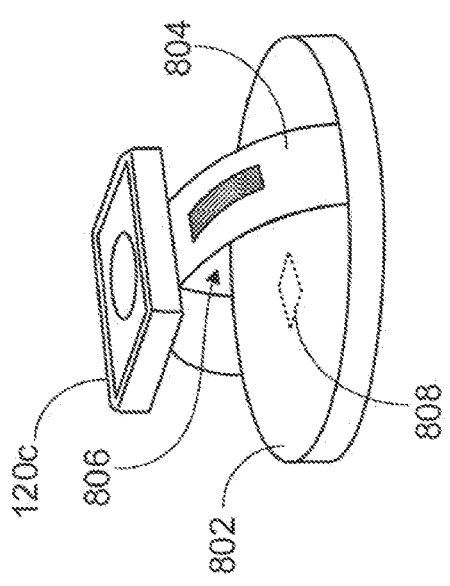

In some cases, the position of the wearable computing device 120c can be adjusted with respect to the plate or pad 802. For example, as shown in FIG. 8B, the wearable computing device 120c can be mounted onto a swivel mechanism 810. The swivel mechanism 810 includes a mounting plate 816 positioned atop a ball and socket joint 818. The wearable computing device 120c is secured to the mounting plate 816 by one or more clips 820 and/or magnets 822, As shown in FIG. 8C, the swivel mechanism 810 is in turn mounted onto the strap 804. Thus, the wearable computing device 120c can be rotated with respect to the pad 802, such that the rescuer (or another user) can more readily view the wearable computing device 120c during the course of treatment, without otherwise adjusting the position of the plate or pad 802.

Figure 8D:
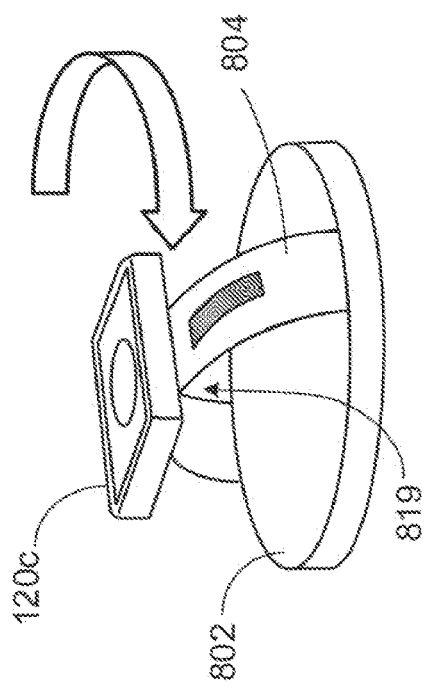
FIG. 8D is a diagram of an example grip or support for the pad or plate shown in FIG. 8A.

In some cases, the plate or pad 802 can include grips or supports that physically guide the user in performing proper chest compressions. For example, as shown in FIG. 8D, the plate or pad 802 (for simplicity, shown without the wearable computing device 120c and straps 804) can include a raised heel 812 to allow the rescuer to rest the heel of the hand against it and position the palm of the hand in proper CPR position. The plate or pad 802 can also include a grip 814 at the front of the plate or pad 802 to prevent slippage of the rescuer's hand. The grip 814 can also include grooves, such that the rescuer can position the fingers in an ergonomic position, thereby rescuing fatigue.

As described above, a user assigned to the respiration monitoring role (i.e., the "respiration monitor") can wear the wearable computing device 120d (corresponding to the respiration monitoring role) to assist him in monitoring the respiration of the patient during the course of treatment.

Figure 9A:
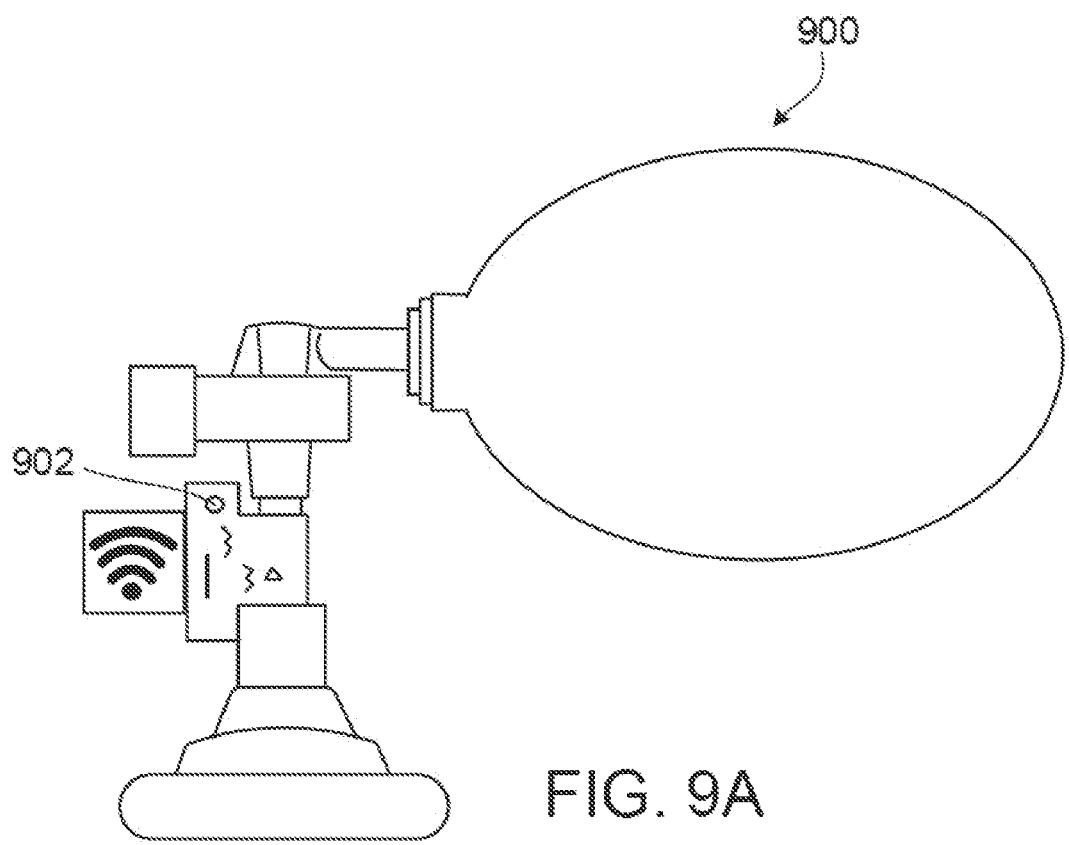
FIG. 9A is a diagram of an example capnometer positioned on a bag valve mask.
Figure 9B:
FIG. 9B is a diagram of an example graphical user interfaces presented by a wearable computing device.

For example, if the patient has adequate blood flow to his lungs, the production of carbon dioxide by the patient's tissues will be appropriately eliminated by the lungs. Hence, elevated levels of end tidal $CO_2$ ($ETCO_2$) can be a reflection of appropriate resuscitation efforts. Referring to FIG. 9A, the wearable computing device 120d can obtain information regarding the $ETCO_2$ of the patient through a capnometer 902 (a sensor for measuring the concentration or partial pressure of $CO_2$) positioned along the airway of a bag valve mask 900. As the respiration monitor operates the bag valve mask 900 to manually provide positive pressure ventilation to the patient, the capnometer 902 obtains sensor measurements regarding the concentration of partial pressure of $CO_2$ of air exhaled from the patient's lungs. The capnometer 902 is communicatively coupled to the wearable computing device 120d (e.g., through a wired or wireless connection), such that the respiration monitor can observe the $ETCO_2$ of the patient. For example, as shown in FIG. 9B, the wearable computing device 120d can present a GUI 900 that displays the $ETCO_2$, along with other information regarding the patient (e.g., the time that was elapsed since the leader initiated intervention). In some cases, the capnometer 902 can be positioned along the airway of an endotracheal tube to measure the $ETCO_2$ of the patient, for example when the patient is intubated. For the patient's $ETCO_2$ is low (e.g., below a particular threshold value, such as 10), the wearable computing device 120d can prompt the user to adjust the respiratory resuscitation. The wearable computing device 120d records and transmits this information to the computing device 110 for storage. The wearable computing device 120d and/or the computing device 110 can also transmit this information to one or more of the other wearable computing devices 120a-c. For example, the wearable computing device 120d and/or the computing device 110 can transmit information indicating that the patient's $ETCO_2$ is low to the wearable computing device 120c, prompting the rescuer to adjust his compression efforts.

Figure 10:
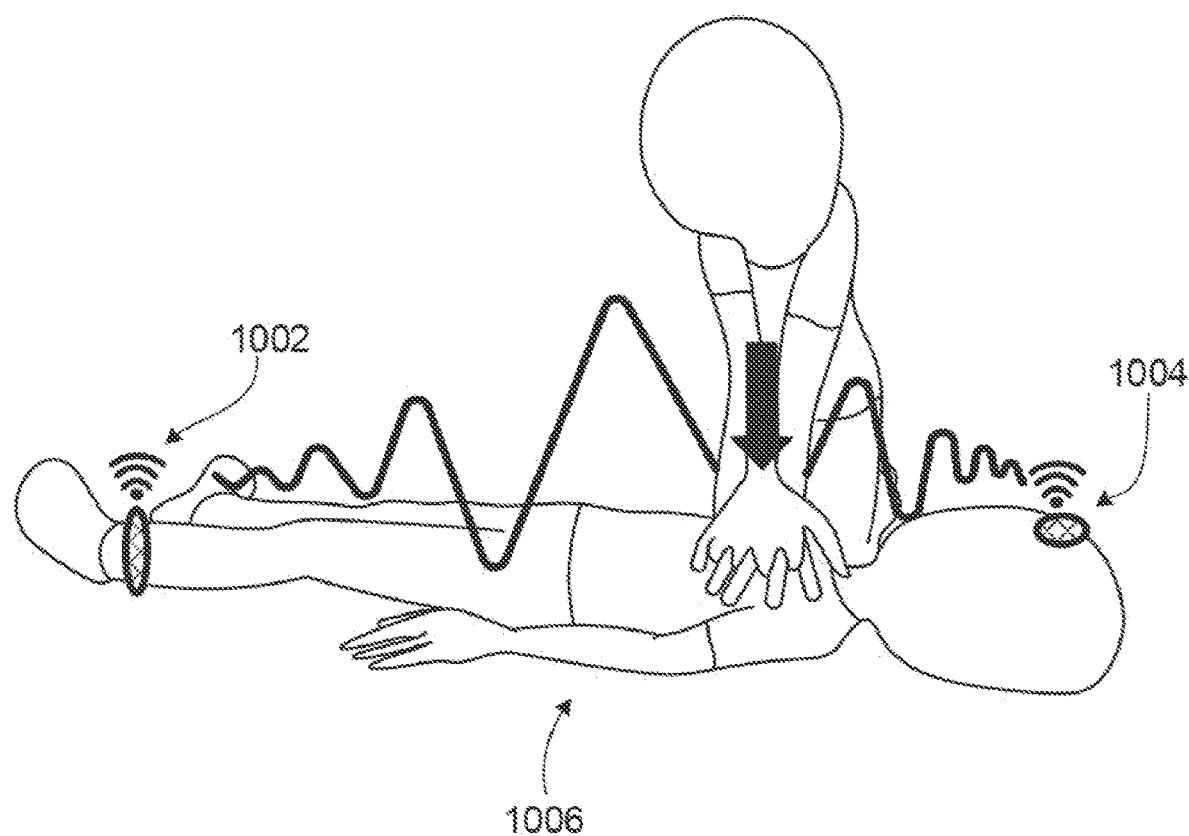
FIG. 10 is a diagram of example sensors for measuring aspects of a patient's condition.

In some implementations, the electronic system 100 can also include one or more additional sensors for measuring other aspects of a patient's condition. For example, referring to FIG. 10, the electronic system 100 can further include sensors 1002 and 1004 that measure a patient's perfusion. The sensors 1002 and 1004 are placed on the patient's body 1006 (e.g., on the extremities of the patient, such as his arms or legs, or his forehead), and measure properties such as the patient's vascular flow or tissue oxygenation. Example sensor include laser Doppler flow sensors (e.g., scanning laser Doppler flowmetry sensors), spectroscopy (NAIR) sensors, and tissue saturation monitors.

Information gathered by the sensors 1002 and 1004 can be transmitted to other components of the electronic system 100 (e.g., the computing system 110 and/or one or more wearable computing devices 120a-d through a wireless network connection) to provide the members of the intervention team with information regarding the patient's condition. For example, in some cases, the information gathered by the sensors 1002 and 1004 can be used to determine the CPR quality index and/or a perfusion quality index. As another example, in some cases, the electronic system 100 can determined, based on information gathered by the sensors 1002 and 1004, that the patient's perfusion is poor. In response, the electronic system 100 can notify one or more of the members of the intervention team (e.g., by presenting an alert or notification using one or more of the wearable computing devices 102a-d) to modify or otherwise improve the resuscitation efforts.

Figure 11A:
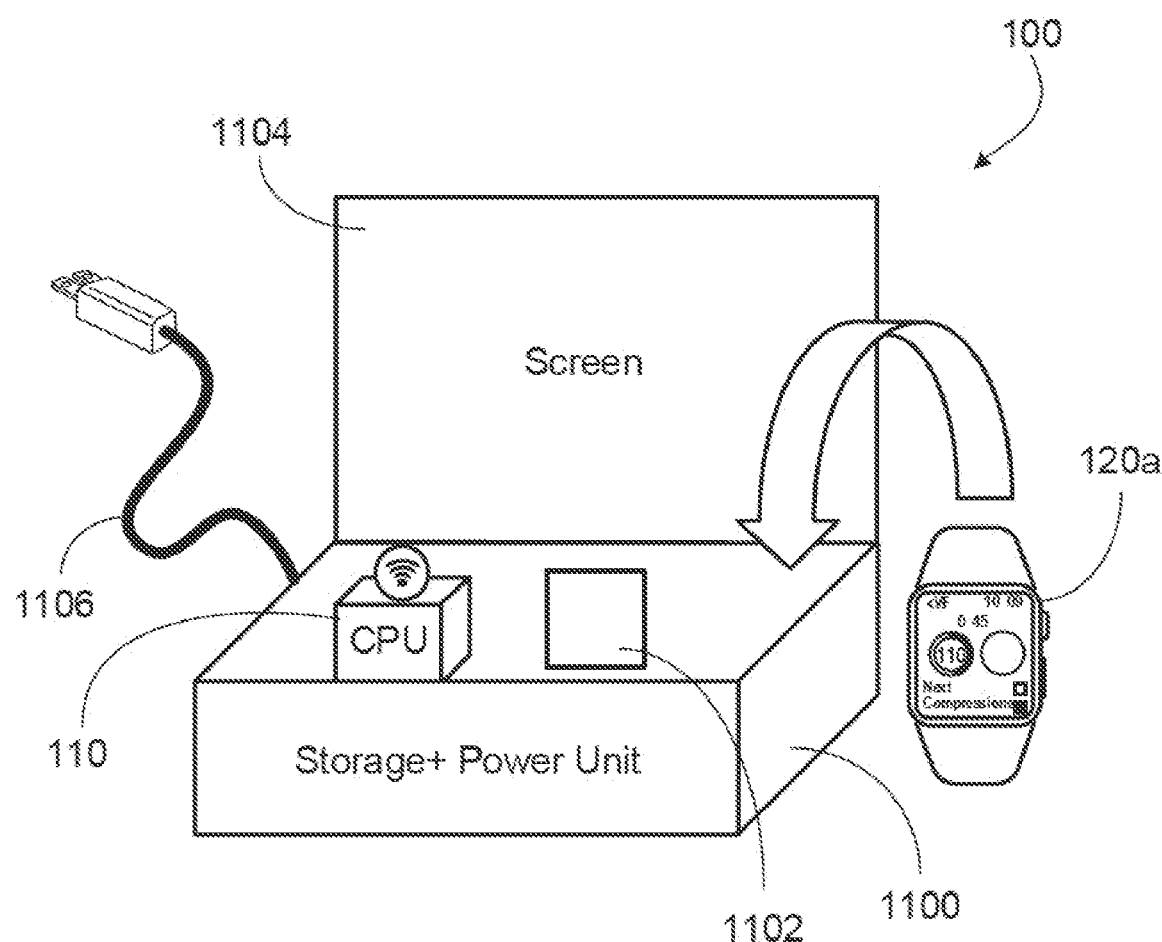
FIG. 11A is a diagram of an example storage container.

In some cases, one or more of the components of the electronic system 100 can be stored in a storage container for convenient organization and transport. For example, as shown in FIG. 11A, the components of the electronics system 100, including the computing system 110 and the wearable watches 120a-d (for simplicity, only a single watch 120a is shown) can be stored in a storage container 1100. This storage container 1100 can be placed in a convenient location, such that the electronic system 100 is readily accessible during an emergency situation. For example, the storage container 1100 can be placed in a patient treatment area, such as a patient's room or an operating room. As another example, the storage container 1100 can be placed on a moveable cart (e.g., a "crash cart"), such that the storage container 1100 can be readily relocated in the event of an emergency. In an emergency situation, members of the intervention team can access the storage container 1100, and take an appropriate wearable computing device 120a-d for use during the patient's treatment.

In some cases, the electronic system 100 can include sensors that measure the compression depth of the rescuer's chest compressions on the patient. This can be beneficial, for example, as it can provide the rescuer (as well as other members of the intervention team) with additional feedback regarding the performance of chest compressions. This information can be obtained in various ways.

Figure 11B:
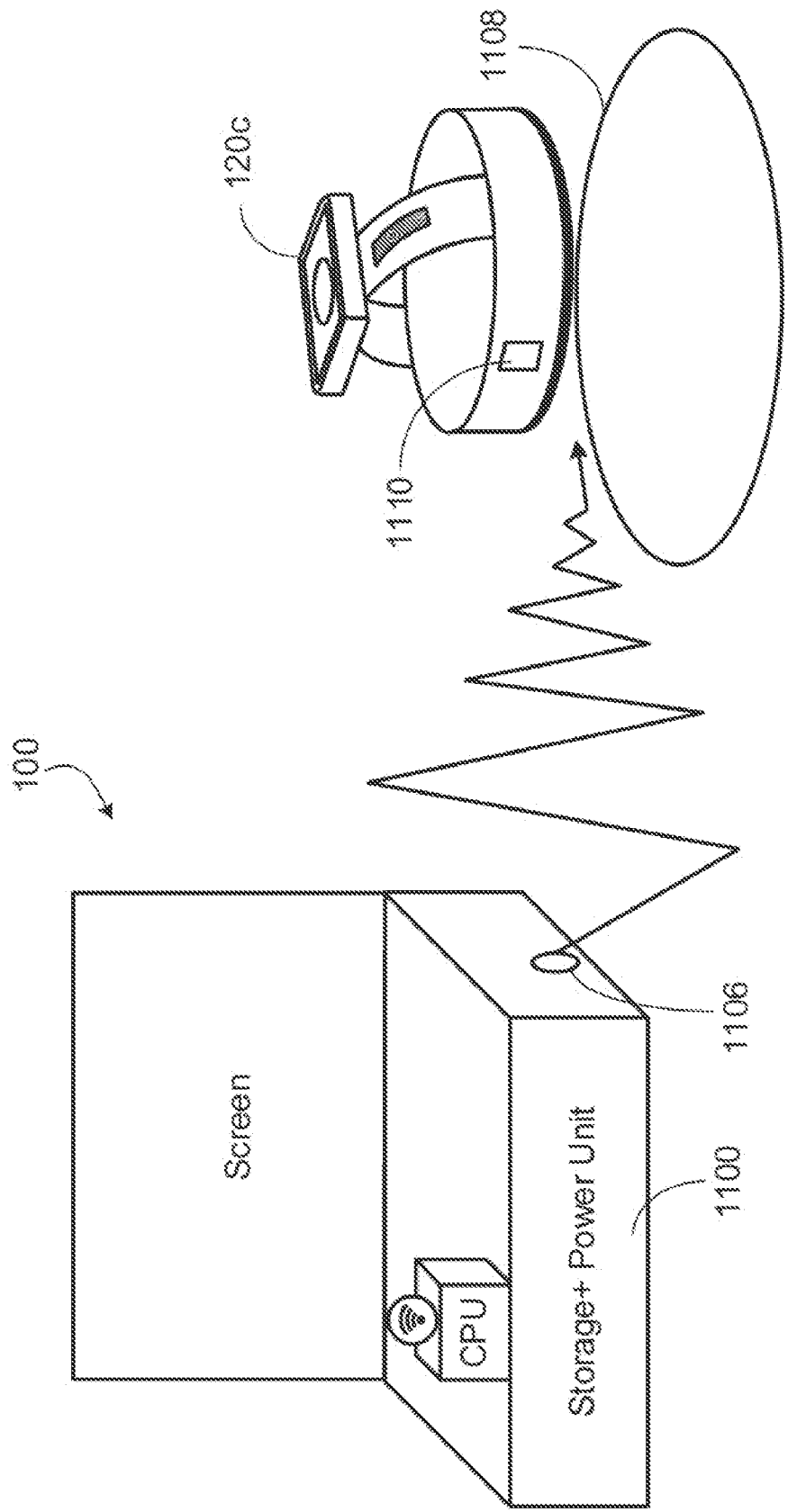
FIG. 11B is a diagram of an example system for measuring the compression depth of a rescuer's chest compressions on a patient.

For example, as shown in FIG. 11B, the storage container 1100 can include a camera 1106 positioned facing the patient's chest 1108. During the course of treatment, the rescuer places the wearable computing device 120c (mounted to the pad or plate 802 through straps 804) atop the patient's chest 1108, and applies chest compressions. The pad or plate 802 includes a visual marker 1110 which is detected by the camera 1106 during treatment. The visual marker 1110 can be, for example, an object or portion of the pad or plate 802 of contrasting color, a light (e.g., an LED), or some other visually detectable feature. As the rescuer compresses the patient's chest, the camera 1106 records the movement of the visual marker 1110. Based on this movement, the electronic system 100 (e.g., via the computing device 110) can calculate the compression depth, and provide the rescuer with feedback regarding his performance (e.g., by transmitting the information to the wearable device 120c for presentation to the user via a network connection). In some cases, a visual reference scale (e.g., a ruler or an object of known size) can be placed near the patient and in view of the camera 1106 to calibrate the compression depth calculations.

As another example, as shown in FIG. 11C, the system 100 can include two proximity sensors 1112a-b. The first proximity sensor 1112a can be placed on the patient's chest 1108, and a second proximity sensor 1112b can be placed beneath the patient's back, opposite the patient's chest 1108. The first and second sensors can detect their proximity to one another; based on this information, the electronic system 100 (e.g., via the computing device 110) can calculate the compression depth, and provide the rescuer with feedback regarding his performance (e.g., by transmitting the information to the wearable device 120c for presentation to the user via a network connection).

In some cases, as shown schematically in FIG. 11D, the proximity sensors 1112a-b can each act as a parallel capacitor plates, and the electronic system 100 can detect their proximity to one another by detecting a change in impedance between the proximity sensors 1112a-b. Based on this change in impedance, the electronic system 100 (e.g., via the computing device 110) can calculate the compression depth, and provide the rescuer with feedback regarding his performance (e.g., by transmitting the information to the wearable device 120c for presentation to the user via a network connection).

As another example, in some cases, the system 100 can include an electromagnetic motion tracking system 1120 to measure the compression depth. As shown in FIG. 11E, electromagnetic motion tracking system 1120 includes a signal generator 1122, a transmit antenna assembly 1124 electrically coupled to the signal generator 1122, and one or more sensors 1126 embedded on or within the wearable computing device 120c (on or within the plate or pad).

During use, the signal generator 1122 applies an electrical current to the transmit antenna assembly to generate a magnetic field (e.g., a near field, low frequency magnetic field having particular known vector characteristics) about the patient's chest 1108. In turn, directional antenna assemblies embedded within each of the sensors 1126 detect the magnetic field, and transmit information regarding the detected magnetic field (e.g., the magnitude and orientation of the detected field) to a computing device (e.g., to the wearable computing device 120c or the computing device 110 through a wired or wireless connection). Based on this information, the system 1120 can determine the position and orientation of each of the sensors with respect to the transmit antenna assembly 1124. Thus, the system 1120 can monitor the changes in position of the sensors 1126 to estimate the movement of the sensors 1126 during treatment, and in turn, estimate the degree to which the patient's chest is compressed during treatment. Electromagnetic motion tracking systems can include, for example, components from Polhemus, Inc. (Colchester, VT), such as G4, Liberty, Patriot, Scout, Liberty Latus, Fastrak, or Patriot Wireless.

Although FIG. 11E depicts the sensors 1126 as embedded on or within the wearable computing device 120c, this is merely an illustrative example. In some cases, the sensors 1126 can be separate from the wearable computing device 120c, and can be independently positioned onto a patient's chest by a caretaker prior to treatment. For example, in some cases, the sensors 1126 can be mounted within a thin discrete housing (e.g., a mat made of a soft or compliant material), and placed between the patient's chest and the wearable computing device 120c prior to a caretaker applying chest compressions. During use, the sensors 1126 detect the magnetic field generated by the antenna assembly 1124, and information regarding the detected magnetic field to a computing device (e.g., via a wired or wireless transceiver communicatively coupled to the sensors).

Other sensors are also possible, depending on the implementation. For example, in some cases, the wearable computing device 120c can include an accelerometer. Based on changes in acceleration, the electronic system 100 (e.g., via the computing device 110) can calculate the compression depth, and provide the rescuer with feedback regarding his performance. In some cases, the compression depth can be calculated through spectral analysis of acceleration measurements obtained by the accelerometer. For example, the accelerometer can obtain a series of measurements over time (signal a(t)). This signal can be approximated as:

$$a(t) = \sum_{k=1}^{N} A_k \cos(2\pi k f_{cc} t + \theta_k).$$

where N is the number of harmonics, $f_{cc}$ is the mean frequency of the compressions (hertz), $A_k$ is the amplitude of the kth harmonic.

Correspondingly, the chest displacement can be approximated as:

$$s(t) = \sum_{k=1}^{N} S_k \cos(2\pi k f_{cc} t + \phi_k),$$

where $$S_k = \frac{1000 A_k}{(2\pi k f_{cc})^2}$$

and $$\phi_k = \theta_k + \pi, \text{ for } k = 1, 2, \ldots, N.$$

To obtain signal s(t), the signal a(t) is transformed via a fast Fourier transform (FFT) to obtain signal A(t). Several harmonics (e.g., the first three harmonics) and their fundamental frequency are determined based on the transformed signal, and are used to estimate the signal s(t) based on the equations above. Accordingly, the rate and depth of the compress compressions can be calculated using the resulting signal s(t) (e.g., by determining the amplitude range of signal s(t) within one or more cycles, and determining the frequency of those cycles). Although an example technique of estimating the compression depth is described, this is merely an illustrative example. Other techniques are also possible, depending on the implementation.

As shown in FIG. 11A, the storage container 1100 also includes a power unit 1102 and a display device 1104. The power unit 1102 provides power to each of the components contained within the storage container 1100. For example, the power unit 1102 can obtain power from an external source (e.g., through a power cord 1106), convert the power as necessary, and deliver the power to the computing system 110. As another example, the power unit 1102 can deliver power to each of the wearable computing devices 120a-d and/or sensors 1002 and 1004 to recharge batteries contained within them. As another example, the power unit 1102 can deliver power to the display device 1104.

The display device 1104 visually presents information to the members of the intervention team. The types of information presented by the display device 1104 can vary, pending on the implementation. For example, in some cases, the display device 1104 can display the same or similar information as that being presented on one or more of the wearable computing devices 120a-d. This can be useful, for example, as it allows each member of the intervention team to quickly view information pertaining to any of the members of the team. As another example, in some cases, the display device 1104 can display a selection of information regarding the patient and/or the treatment procedure (e.g., the amount of time that has elapsed since the leader initiated the intervention, vital signs of the patients, the next task to be performed by a member of the team, the last task that was performed, and so forth). As another example, in some cases, the display device 1104 can display historical information (e.g., historical charts or graphs of information regarding the treatment—such as a time-dependent graph of the CPR quality index, the perfusion quality index, and/or information regarding the patient—such as a time-dependent graph of the patient's vital signs).

In some cases, the storage container 1100 can automatically engage or disengage the electronic system 100 when it is accessed. For example, in some cases, the display device 1104 can be mounted on a hinge or other articulating mechanism, such that it can open and close to reveal the wearable computing devices 120a-d stored within the storage container 1100. When the display device 1104 is swung open, the storage container 1100 can power up and/or initiate operation of the computing system 110, the wearable computing devices 120a-d, and/or the display device 1104, such that each are ready for use. This can be beneficial, for example, as it allows members of the intervention team to quickly access and operate the electronic system 100 in the event of an emergency.

In some cases, the information displayed on the wearable computing devices 120*a-d* and/or the display device 1104 can be color coded, such that users can more readily understand the presented information. For example, in some cases, information related to defibrillation can be color coded yellow. As another example, information related to medication administration-related events including timers, doses, and so forth can be color coded blue. As another example, information such as compression timers and alerts can be color coded red. As another example, green can be used to indicate that parameters are within an acceptable range, and to indicate information related to capnometer readings. In practice, other combinations of colors and information can be used, depending on the implementation.

Although implementations of electronic system 100 are shown often, these are merely illustrative examples. In practice, the electronic system 100 can differ, depending on the implementation.

For example, although the electronic system 100 is described as having four wearable electronic devices 120*a-d*, the number of wearable electronic devices can vary. For example, in some cases, there may be additional roles in addition to or instead of those described. Thus, there may be one or more wearable electronic devices corresponding to each of those roles. Similarly, in some cases, more than one wearable electronic devices may correspond to some or all of the roles. This can be beneficial, for example, if multiple people are assigned to the same role as a team.

Further, not all wearable electronic devices 120*a-d* need be used simultaneously. For instance, in some cases, one or more of the roles may be left unfilled, and the responsibilities and tasks associated with those roles can be assigned to other members of the intervention team and/or automatically performed by the electronic system 100. As an example, in some cases, an intervention team might not have a recorder. Thus, the tasks associated with the recorder can be assigned to other members of the team (e.g., the leader) and/or automatically performed (e.g., by automatically recording the occurrence of each event without user intervention). In this manner, the electronic system 100 can provide members of the team with information regarding their tasks, regardless of the number and members available to assist in a given situation.

Further, in some cases, the computing device 110 need not be present. Instead, the functionality of the computing device 110 can instead be performed by one or more of the wearable computing devices 120*a-d*. For example, in some cases, the wearable computing device 120*a* receives information from each of the other wearable computing devices 120*b-d*, and stores the received information for future retrieval. Thus, in these cases, the wearable computing device 120*a* can act as a central location for the storage of information collected by the system 100.

Further, in some cases, the wearable computing device 120*c* can be used independently from the other devices of the system 100. For example, the wearable computing device 120*c* can provide a user with instructions for treating a patient in cardiac arrest without the assistance of others, provide feedback to the user during the course of treatment, and call others for assistance. This can be beneficial, for example, in situations where a full medical intervention team is not immediately available to assist the patient. This can also be useful, for example, in a home, office, or public setting (e.g., a restaurant, theater, store, or so forth), where those who are immediately available to assist the patient may be lay people, and may lack to experience needed to treat the patient without guidance.

In these cases, the wearable computing device 120*c* can perform some or all of the functions that might otherwise be performed by other components of the system 100. For example, the wearable computing device 120*c* can retrieve information regarding one or more treatment protocols suitable for a single person to perform. The wearable computing device 120*c* can provide the user with information regarding when to perform each of the tasks to the protocol, the proper time at which to perform those steps.

Further, the wearable computing device 120*c* can provide instructions to assist the user in performing the tasks. For instance, the wearable computing device 120*c* can present the user with text, images, videos, animations, spoken information, and/or audio cues that guide the user in performing each task. As examples, the wearable computing device 120*c* can present the user with text and audio prompting the user to take the patient's pulse, present the user with and text and animation regarding the proper technique for doing so. The wearable computing device 120*c* can also present spoken instructions that guide the user through each steps of the technique. Further, the wearable computing device 120*c* can prompt the user for input regarding the outcome of the technique, such that it can determine which task should be performed next. In this manner, the user is guided through the entire treatment process.

In some cases, the wearable computing device 120*c* can also provide the user with feedback regarding his performance, and if needed, instruct the user in adjusting his efforts. For example, the wearable computing device 120*c* can determine whether the user is applying a proper amount of pressure during chest compressions, and whether the user is applying chest compressions at the proper rate. If the user is not performing in accordance with the protocol, the wearable computing device 120*c* can instruct the user to adjust his performance, and provide instructions for making those adjustments.

In some cases, the wearable computing device 120*c* can also record the performance of the user during the treatment process. For example, the wearable computing device 120*c* can record which tasks were performed by the user, the time at which those tasks were performed, and information regarding the performance of those tasks (e.g., the amount of pressure applied, the rate at which chest compressions were applied, and so forth). This information can be accessed later to assess the user's performance and/or to provide caretakers with additional information that could be useful in treating the patient in the future.

In some cases, the wearable computing device 120*c* can also call others for assistance. For example, the wearable computing device 120*c* can transmit a message to an emergency call center, hospital, a fire station, and/or a police station, notifying the recipients that an emergency situation is in progress. The message can be, for example, a text message (e.g., SMS message), an e-mail, an instant message, a telephone call, a facsimile, or other message. In some cases, the wearable computing device 120*c* can also transmit its location (e.g., by obtaining location information using a GPS sensor). This can be useful, for example, as it frees the user to immediately treat the patient without delay. Additionally it allows the rescuer to perform resuscitation tasks without the need to hold a telephone and can therefore receive instructions from a dispatcher without interrupting compressive efforts. This can also be useful, for example, as it automatically notifies others of the situation, without relying on a user who might otherwise forget or delay initiating the notification process to others.

FIGS. 12A-C show example GUIs 1200a-c that can be displayed to the user during the notification process. For example, as shown in FIG. 12A, the wearable computing device 120c can present a GUI 1200a indicating that an emergency call should be placed. As shown in FIG. 12B, the wearable computing device 120c can present a GUI 1200b confirming to the user that the emergency call is being placed. As shown in FIG. 12C, the wearable computing device 120c can present a GUI 1200c indicating that that the call is connected. In this manner, the wearable computing device 120a-c can inform the user of each step of an emergency, and can keep the user apprised of the call's status.

Figure 13:
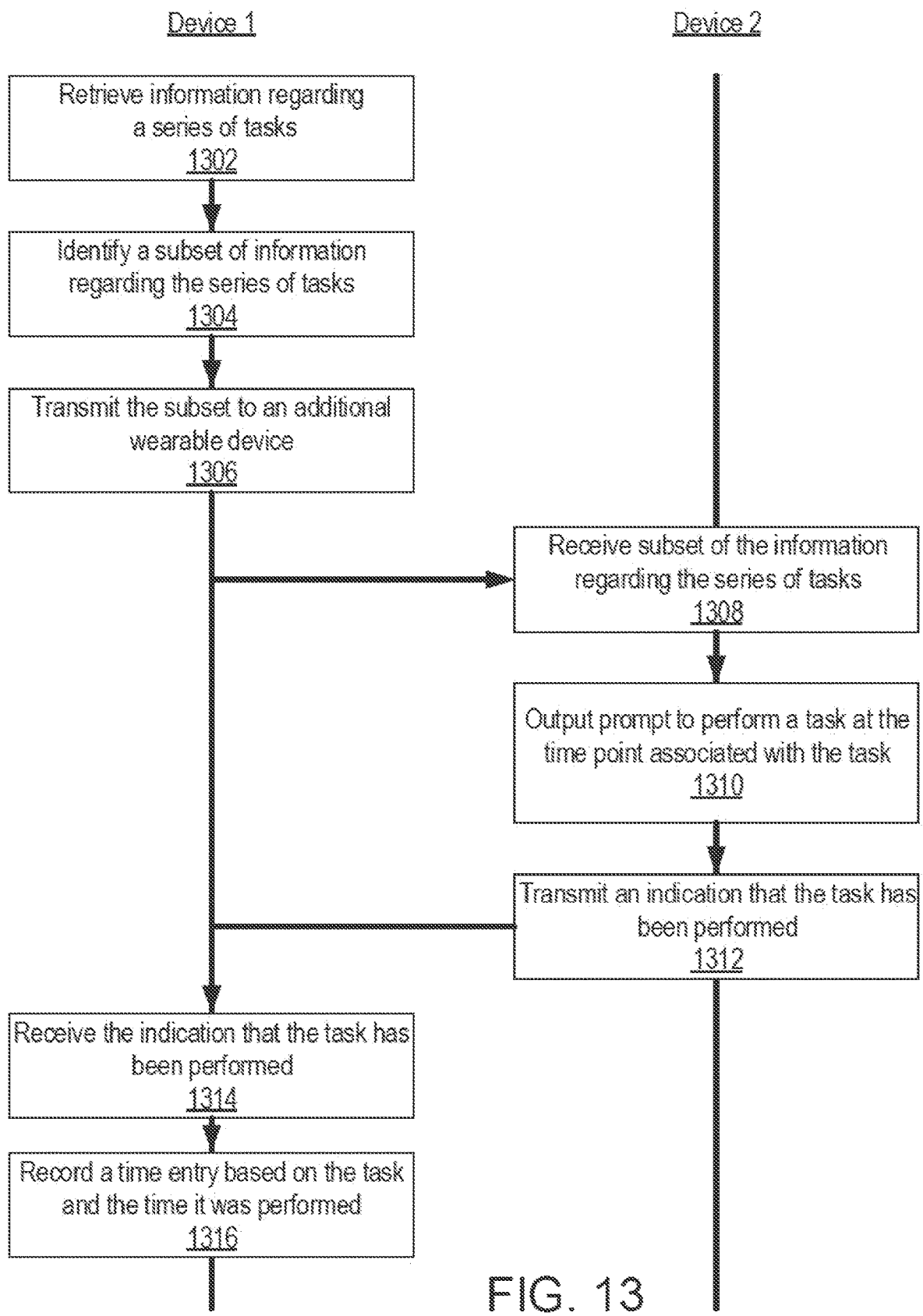
FIG. 13 is a flowchart diagram of an example process for assisting users in performing medical procedures.

FIG. 13 is a flowchart of an example process 1300 for assisting one or more users in treating a patient in cardiopulmonary arrest. In this simplified example, the steps performed by two wearable computing devices are described. However, it is understood that the steps can be performed by more than two wearable computing device (e.g., three, four, or more). The process 1300 begins by a first wearable computing device (e.g., wearable computing device 120a) retrieving information regarding a series of tasks to be performed in treating a patient in cardiopulmonary arrest (step 1302). This information can include, for example, information regarding one or more intervention protocols that an intervention team can follow to treat the patient. Information regarding each protocol can be retrieved, for example, from an external computer system (e.g., a computing system 110), and/or pre-stored on the first wearable computing device. Each tasks can be a task that is performed to treat the patient in cardiopulmonary arrest. Example tasks include measurement of a pulse of the patient, administration of a drug to the patient, performance of chest compressions on the patient, and performance of a defibrillating shock to the patient.

The information regarding the series of tasks can include information regarding each of the tasks. For example, the information can include, for each task, a description of the task, instructions for performing the task, an indication of a user that is assigned to perform the task, and/or an indication to perform the task at a particular time.

The first wearable computing device then identifies a subset of the information regarding the series of tasks (step 1304), and transmit the subset of information to a second wearable computing device (e.g., a wearable computing device 120b-c) (step 1306). In some cases, the subset of information can pertain to a particular task assigned to the wearer of the second wearable computing device. For example, the subset of information can include a description of the task to be assigned to the wearer of the second wearable computing device, instructions for performing that task, and/or an indication to perform the task at a particular time. The subset of information can be transmitted over a suitable communications network (e.g., a Wi-Fi network, a Bluetooth network, a NFC network, and so forth).

In response, the second wearable computing device receives the subset of the information regarding the series of tasks (step 1308), and outputs a prompt to perform a task at the time point associated it the task (step 1310). The task can be, for example, the task assigned to the user of the second wearable computing device. The prompt can include, for example, a visual indication (e.g., an image, text, an animation, a "pop-up," a change in color, or other visual indication), an audible indication (e.g., a sound effect, music, or other audible indication), and/or a haptic indication (e.g., a vibration). The prompt can also include, for example, a description of the task to be performed and/or instructions to performing the task.

The second wearable computing then transmits an indication that the task has been performed (step 1312). The indication can include, for example, a name of description of the task performed, a time at which the task was performed, and/or further information regarding the task (e.g., one or more performance parameters associated with the task). In some cases, the second wearable computing device can determine that the task has been performed based an input from a user (e.g., a wearer of the first wearable computing device, the wearer of a second wearable computing device, or other user). The indication can be transmitted over a suitable communications network.

In response, the first wearable computing device receives the indication (step 1314), and records a time entry based on the task and the time it was performed (step 1316). For example, the first wearable computing device can record a name of description of the task performed, a time at which the task was performed, and/or further information regarding the task in a storage device located on the first wearable computing device, or on a storage device located external to the first wearable computing device (e.g., a computing device 110).

Although process 1300 describes the steps performed by two wearable computing devices, this is a merely a simplified example to demonstrate the concept. In practice, these steps can be performed by more than two wearable computing devices. For example, the process 1300 can be performed by four wearable computing devices. The first wearable computing device (e.g., the wearable computing device 120a) can retrieve information regarding a series of tasks. The information can include, for each task, an indication of a particular user from among several users to perform the task, an indication of a time point for that particular user to perform the task.

Based on this information, the first wearable computing device can identify multiple subsets of information regarding the tasks, each subset of information corresponding to a different one of the tasks. The first wearable computing device can identify which steps are assigned to which wearers of the other wearable computing devices (e.g., wearable computing devices 120b-d), and transmit each subset of information to the appropriate wearable computing device.

In response, each of the additional wearable computing devices receives the respective subset of information, and outputs a prompt to its wearer perform a task at the time point associated it the task. Each additional wearable computing device then transmits an indication that the task has been performed to the first wearable computing device. In response, the first wearable computing device receives the indications, and record time entries based on the tasks and the time they were performed.

Some implementations of subject matter and operations described in this specification can be implemented in digital electronic circuitry, or in computer software, firmware, or hardware, including the structures disclosed in this specification and their structural equivalents, or in combinations of one or more of them. For example, in some implementations, computing device 110 and wearable computing devices 120a-d can be implemented using digital electronic circuitry, or in computer software, firmware, or hardware, or in combinations of one or more of them. In another example, process 1300 can be implemented using digital electronic circuitry, or in computer software, firmware, or hardware, or in combinations of one or more of them.

Some implementations described in this specification can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 14:
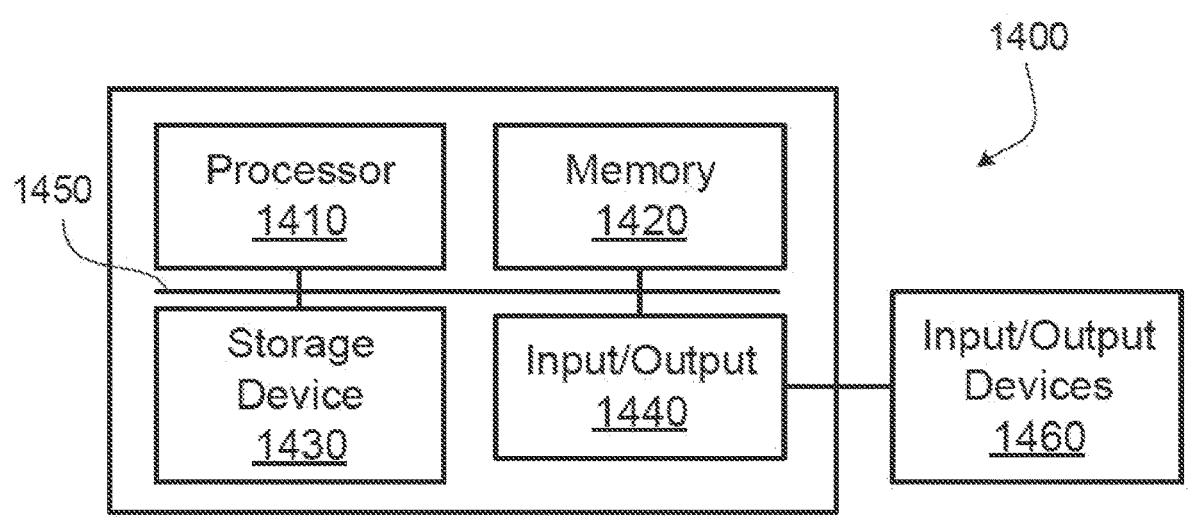
FIG. 14 is a diagram of an example computer system.

FIG. 14 shows an example computer system 1400 that includes a processor 1410, a memory 1420, a storage device 1430 and an input/output device 1440. Each of the components 1410, 1420, 1430 and 1440 can be interconnected, for example, by a system bus 1450. The processor 1410 is capable of processing instructions for execution within the system 1400. In some implementations, the processor 1410 is a single-threaded processor, a multi-threaded processor, or another type of processor. The processor 1410 is capable of processing instructions stored in the memory 1420 or on the storage device 1430. The memory 1420 and the storage device 1430 can store information within the system 1400.

The input/output device 1440 provides input/output operations for the system 1400. In some implementations, the input/output device 1440 can include one or more of a network interface devices, e.g., an Ethernet card, a serial communication device, e.g., an RS-232 port, and/or a wireless interface device, e.g., an 802.11 card, a 3G wireless modem, a 4G wireless modem, etc. In some implementations, the input/output device can include driver devices configured to receive input data and send output data to other input/output devices, e.g., keyboard, printer and display devices 1460. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable subcombination.

A number of implementations have been described. Nevertheless, it will be understood that various modifications may be made without departing from the spirit and scope of the invention. Accordingly, other implementations are within the scope of the following claims.

What is claimed is:

1. A system comprising a plurality of mobile computing devices,
   wherein each mobile computing device is configured to output information regarding a different corresponding subset of tasks of a medical treatment protocol that comprises specific treatment tasks to be performed by users of the plurality of mobile computing devices with respect to treating an individual or as part of a training or education tool and comprises times at which to perform the specific treatment tasks,
   wherein a first mobile computing device of the plurality of mobile computing devices is configured to output information regarding a first subset of tasks of the medical treatment protocol, the first subset of tasks being associated with a leader role in the medical treatment protocol,
   wherein the first mobile computing device is further configured to wirelessly communicate with each other mobile computing device of the plurality of mobile computing devices, and
   wherein a second mobile computing device of the plurality of mobile computing devices is configured to:
      output, for at least one task of a second subset of tasks, a corresponding prompt to perform the at least one task at a respective time point associated with the at least one task;
      record data associated with the at least one task being performed; and
      subsequent to each task of the at least one task being performed, transmit to the first mobile computing device a notification that the task has been performed.

2. The system of claim 1, wherein the second mobile computing device is configured to:
   receive an indication that the at least one task has been performed at a particular time; and
   responsive to receiving the indication that the at least one task has been performed at the particular time,
   record a time entry identifying when the at least one task has been performed; and
   transmit the time entry to the first mobile computing device.

3. The system of claim 1, further comprising:
   a sensor,
   wherein the second mobile computing device is configured to:
      obtain a measurement from the sensor,
      determine, based on the measurement from the sensor, a depth of chest compression caused by movement of the sensor, and
      transmit a value representative of the depth of chest compression.

4. The system of claim 1, further comprising a sensor and an electronic control module in communication with the sensor,
   wherein the electronic control module is configured to, following the output of the corresponding prompt to perform the at least one task, obtain a measurement signal from the sensor.

5. The system of claim 4, wherein the sensor is a capnometer, and wherein the measurement signal indicates a concentration of carbon dioxide exhaled by the individual or a subject of the training or the education tool.

6. The system of claim 4, wherein the sensor is an oxygen sensor, and wherein the measurement signal indicates an oxygen perfusion of the individual or a subject of the training or the education tool.

7. The system of claim 1, wherein the second subset of tasks includes one or more of: measurement of a pulse of a patient, administration of a drug to the patient, performance of chest compressions on the patient, and performance of a defibrillating shock to the patient.

8. The system of claim 1, wherein the information regarding each of the first subset of tasks and the second subset of tasks comprises, for one or more tasks:
   a description of the one or more tasks, and
   instructions for performing the one or more tasks.

9. The system of claim 1, wherein the first mobile computing device is further configured to determine a performance quality index based on information received from the second mobile computing device.

10. The system of claim 1, wherein the first mobile computing device is configured to receive, from the second mobile computing device, information pertaining to administration of a drug.

11. The system of claim 1, wherein the first mobile computing device, the second mobile computing device, or both the first and second mobile computing device are configured to output, to a display, information related to medication administration.

12. The system of claim 1, wherein the first mobile computing device is configured to re-assign one or more tasks of the medical treatment protocol to a different member of an intervention team utilizing the plurality of mobile computing devices.

13. The system of claim 1, wherein the first mobile computing device, the second mobile computing device, or both the first mobile computing device and the second mobile computing device are configured to transmit, receive, or both transmit and receive information relating to treatment of a patient to a computing device remote from the first mobile computing device and the second mobile computing device.

14. The system of claim 13, wherein the information relating to treatment of the patient comprises information regarding a potential treatment protocol.

15. The system of claim 13, wherein the information relating to treatment of the patient comprises information regarding a patient record.

16. The system of claim 13, wherein the information relating to treatment of the patient comprises information related to a performance of a user of the first mobile computing device or the second mobile computing device.

17. The system of claim 13, wherein the information relating to the treatment of the patient comprises any one or more of: an amount of time that has elapsed since an intervention with the patient has been initiated, vital signs of the patient, a next task to be performed by a member of an intervention team utilizing the plurality of mobile computing devices, or a last task performed by the member of the intervention team.

18. The system of claim 1, wherein the first mobile computing device, the second mobile computing device, or both the first and second mobile computing device are configured to output, to a display, information relating to treatment of a patient, wherein the information relating to treatment of the patient comprises any one or more of: an amount of time that has elapsed since an intervention with the patient has been initiated, vital signs of the patient, a next task to be performed by a user of the first mobile computing device or of the second mobile computing device, or a last task performed by the user of the first mobile computing device or of the second mobile computing device.

19. The system of claim 1, wherein the first mobile computing device is configured to:
output a plurality of different diagnostic choices, each diagnostic choice corresponding to a different condition of a patient;
receive a selection of a diagnosis; and
responsive to receiving the selection, specify a course of treatment for the patient.

20. The system of claim 1, wherein the first mobile computing device, the second mobile computing device, or both the first mobile computing device and the second mobile computing device are configured to transmit information relating to performance of a user of a respective mobile computing device of the plurality of mobile computing devices during execution of the medical treatment protocol.

21. The system of claim 20, wherein the performance of the user comprises a set of tasks performed by the user of the respective mobile computing device, a time at which the set of tasks were performed by the user of the respective mobile computing device, and details about how the user of the respective mobile computing device performed the set of tasks.

22. The system of claim 20, wherein the performance of the user of the respective mobile computing device comprises one or more of: information regarding a patient's care during execution of the medical treatment protocol, an identification of tasks that were performed during execution of the medical treatment protocol, or a timing of when tasks were performed during execution of the medical treatment protocol.

23. The system of claim 1, wherein the first mobile computing device is configured to derive a score characterizing a condition of a patient.

24. The system of claim 23, wherein the score comprises a perfusion quality index.

25. The system of claim 23, wherein the first mobile computing device is configured to derive the score based on a carbon dioxide concentration level.

26. The system of claim 23, wherein the first mobile computing device is configured to derive the score based on a vascular flow rate.

27. The system of claim 23, wherein the first mobile computing device is configured to output a prompt in response to determining that a task is not being performed effectively or safely based on the score.

28. The system of claim 27, wherein the prompt comprises instructions for improving performance of the task.

29. The system of claim 28, wherein the instructions for improving performance of the task comprise instructions to slow down or speed up chest compressions.

30. The system of claim 28, wherein the instructions for improving performance of the task comprise instructions to apply more pressure or less pressure during chest compressions.

31. The system of claim 27, wherein determining that the task is not being performed effectively or safely comprises identifying that the score satisfies a threshold condition for a threshold period of time.

32. The system of claim 31, wherein the threshold period of time is 5 seconds or longer.

33. The system of claim 31, wherein the threshold period of time is 15 seconds or longer.

34. The system of claim 1, wherein the first mobile computing device, the second mobile computing device, or both the first mobile computing device and the second mobile computing device are configured to transmit a message to at least one of an emergency call center, hospital, a fire station, or a police station.

35. The system of claim 34, wherein the first mobile computing device, the second mobile computing device, or both the first mobile computing device and the second mobile computing device are configured to transmit location information.

36. The system of claim 1, wherein the first mobile computing device, the second mobile computing device, or both the first mobile computing device and the second mobile computing device are configured to receive patient information from a patient intake system, a hospital notification system, or an emergency code notification system.

37. The system of claim 36, wherein the first mobile computing device is configured to output a cardiac arrest notification based on the patient information.

38. The system of claim 37, wherein the cardiac arrest notification comprises a patient location, a time at which cardiac arrest of a patient began, or a combination of the patient location and the time at which cardiac arrest of the patient began.

39. The system of claim 1, wherein the plurality of mobile computing devices comprises at least one wearable device.

* * * * *